US012697368B2

(12) United States Patent
Day et al.

(10) Patent No.: US 12,697,368 B2
(45) Date of Patent: Aug. 4, 2026

(54) TSG6 POLYPEPTIDE FRAGMENT FOR DRY EYE DISEASE

(71) Applicant: The University of Manchester, Manchester (GB)

(72) Inventors: Anthony Day, Manchester (GB); Caroline Milner, Manchester (GB); Joo Youn Oh, Seoul (KR)

(73) Assignee: THE UNIVERSITY OF MANCHESTER, Manchester (GB)

( * ) Notice: Subject to any disclaimer, the term of this patent is extended or adjusted under 35 U.S.C. 154(b) by 694 days.

(21) Appl. No.: 17/597,802

(22) PCT Filed: Jun. 23, 2020

(86) PCT No.: PCT/EP2020/067448
§ 371 (c)(1),
(2) Date: Jan. 24, 2022

(87) PCT Pub. No.: WO2021/013452
PCT Pub. Date: Jan. 28, 2021

(65) Prior Publication Data
US 2022/0288161 A1     Sep. 15, 2022

(30) Foreign Application Priority Data

Jul. 25, 2019     (GB) ..................................... 1910645

(51) Int. Cl.
| | |
|---|---|
| *A61K 38/17* | (2006.01) |
| *A61K 9/00* | (2006.01) |
| *A61K 31/4725* | (2006.01) |
| *A61K 31/573* | (2006.01) |
| *A61K 38/13* | (2006.01) |
| *A61P 27/02* | (2006.01) |
| *A61P 27/04* | (2006.01) |
| *A61P 37/06* | (2006.01) |

(52) U.S. Cl.
CPC ........ *A61K 38/1709* (2013.01); *A61K 9/0048* (2013.01); *A61K 31/4725* (2013.01); *A61K 31/573* (2013.01); *A61K 38/13* (2013.01); *A61P 27/04* (2018.01); *A61P 37/06* (2018.01)

(58) Field of Classification Search
CPC .............. A61K 38/1709; A61K 9/0048; A61K 31/4725; A61K 31/573; A61K 38/13; A61P 27/04; A61P 37/06; A61P 27/02; A61P 9/08; C07K 14/4718
See application file for complete search history.

(56) References Cited

U.S. PATENT DOCUMENTS

| | | |
|---|---|---|
| 9,062,103 B2 | 6/2015 | Prockop et al. |
| 9,878,003 B2 | 1/2018 | Day et al. |
| 2003/0023406 A1 | 1/2003 | Kataoka |
| 2006/0239965 A1* | 10/2006 | Szoka ...................... B82Y 5/00 |
| | | 514/8.4 |
| 2009/0099084 A1 | 4/2009 | Sabokbar et al. |
| 2015/0057229 A1 | 2/2015 | Day et al. |
| 2016/0075750 A1 | 3/2016 | Prockop et al. |
| 2016/0297854 A1 | 10/2016 | Ghosh et al. |
| 2017/0291939 A1 | 10/2017 | Di Padova et al. |
| 2020/0038521 A1 | 2/2020 | Trippel et al. |
| 2020/0103418 A1 | 4/2020 | Hackney et al. |
| 2025/0121028 A1 | 4/2025 | Day et al. |

FOREIGN PATENT DOCUMENTS

| | | |
|---|---|---|
| CN | 104995303 A | 10/2015 |
| EP | 2001499 B1 | 6/2013 |
| WO | 2007/101988 A2 | 9/2007 |
| WO | 2011/139357 A1 | 11/2011 |
| WO | 2013/067133 A1 | 5/2013 |
| WO | 2015/084706 A1 | 6/2015 |
| WO | 2015/094846 A2 | 6/2015 |
| WO | 2018/165218 A1 | 9/2018 |
| WO | 2021/013452 A1 | 1/2021 |
| WO | 2022/157181 A1 | 7/2022 |

OTHER PUBLICATIONS

Lin et al., "dry eye disease: review of diagnostic approaches and treatments," Saudi Journal of ophthalmology 28:173-181 (2014) (Year: 2014).*
Introduction to Corneal Disorders, Merck manuals, accessed Sep. 20, 2021 at URL merckmanuals.com/professional/eye-disorders/corneal-disorders/introduction-to-corneal-disorders?query=corneal disorders (Year: 2021).*
Corneal Ulcer, Merck manuals, accessed Sep. 2021 at URL merckmanuals.com/professional/eye-disorders/corneal-disorders/corneal-ulcer (Year: 2021).*
Keratoconus, Merck manuals, accessed Sep. 20, 2021 at URL merckmanuals.com/professional/eye-disorders/corneal-disorders/keratoconus (Year: 2021).*
Corneal dystrophies, accessed Jan. 2, 2025 at URL nei.nih.gov/learn-about-eye-health/eye-conditions-and-diseases/corneal-conditions/corneal-dystrophies (Year: 2025).*
Drumm et al, Genetic Variation and Clinical Heterogeneity in Cystic Fibrosis, Annu. Rev. Pathol. Mech. Dis., 2012, 7, pp. 267-282 (Year: 2012).*
Yampolsky et al, The Exchangeability of Amino Acids in Proteins, Genetics, 2005, 170, pp. 1459-1472. (Year: 2005).*
Thia et al, "New developments in the management of persistent corneal epithelial defects," Survey Opthalmol. 68:1093-1114 (2023) (Year: 2023).*
International Search Report and Written Opinion for International Application No. PCT/EP2020/067448, entitled "TSG6 Polypeptide Fragment for Dry Eye Disease," consisting of 14 pages. Date of Mailing: Sep. 23, 2020.
Day, et al., "TSG-6: A Multifunctional Protein with Anti-Inflammatory and Tissue-Protective Properties," Matrix Biol. 78-79, 60-83 (2019).

(Continued)

*Primary Examiner* — Julie Ha
*Assistant Examiner* — Kristina M Hellman
(74) *Attorney, Agent, or Firm* — HAMILTON, BROOK, SMITH & REYNOLDS, P.C.

(57) ABSTRACT

Described herein is a treatment of dry eye disease and particularly, although not exclusively, to the treatment of dry eye disease with a LINK_TSG6 polypeptide.

9 Claims, 24 Drawing Sheets

Specification includes a Sequence Listing.

(56) References Cited

OTHER PUBLICATIONS

Kim et al., "Comparison of Topical Application of TSG-6, Cyclosporine, and Prednisolone for Treating Dry Eye," Cornea, 35:536-542 (2016).

Ghosh et al., "Long acting protein drugs for the treatment of ocular diseases," Nature Communications, pp. 1-15 (2017).

Day, A.J. et al., "TSG-6: A Multifunctional Protein with Anti-Inflammatory and Tissue-Protective Properties," Matrix Biol. 78-79: 60-83 (2018).

Day, J et al: "A novel chondroprotective property of TSG-6 has therapeutic potential for OA." Osteoarthritis and Cartilage vol. 24 (Apr. 1, 2016).

Emami, A. et al., "Toxicology Evaluation of Drugs Administered via Uncommon Routes: Intranasal, Intraocular, Intrathecal/Intraspinal and Intra-Articular," Int J Toxicol, 37(1): 4-27 (2018).

Ghosh, J.G. et al., "Long acting protein drugs for the treatment of ocular diseases," Nature Communications, pp. 1-15 (2017).

International Search Report and Written Opinion for International Application No. PCT/EP2022/051101, entitled "Use of Link-TSG6 for the Treatment of Osteoarthritic Pain," consisting of 10 pages. Date of Mailing: Apr. 28, 2022.

International Search Report and Written Opinion received for PCT Patent Application No. PCT/EP22/051101, mailed on Apr. 28, 2022, 10 pages.

Kim, Y.J. et al., "Comparison of Topical Application of TSG-6, Cyclosporine, and Prednisolone for Treating Dry Eye," Cornea, 35:536-542 (2016).

Kotwal, N. et al., Quantitative Analysis of Mouse Articular Cartilage using Equilibrium Partitioning of Ionic Contrast Agent via Micro Computed Tomography (EPIC-uCT), ORS 2011 Annual Meeting, Paper No. 214, 1 page (2011).

Ichiseki, T. et al., "Intraarticularly-Injected Mesenchymal Stem Cells Stimulate Anti-Inflammatory Molecules and Inhibit Pain Related Protein and Chondrolytic Enzymes in a Monoiodoacetate-Induced Rat Arthritis Model," International Journal of Molecular Sciences, 19, 203, 12 pages (2018).

Wehr, B. et al., "Tibial Cartilage Surface Area, Thickness and Volume in Various Animal Species and in Humans," Osteoarthritis and Cartilage, vol. 15, abstract, 2 pages (No Date Given).

Yang, H. et al., "Anti-inflammatory protein TSG-6 secreted by bone marrow mesenchymal stem cells attenuates neuropathic pain by inhibiting the TLR2/MyD88/NF-kB signaling pathway in spinal microglia," Journal of Neuroinflammation, 17(1): 21 pages (2020).

Bo-Li Zhang et al., Common general knowledge: Guidelines for Rational Clinical Use of Chinese Patent Medicines in Common Diseases: Opthalmology, Jul. 31, 2015, Huaxia Publishing House.

Fu et al. "Osteoarthritis: the genesis of pain", Rheumatology, vol. 57, No. suppl_4, Dec. 15, 2017 (Dec. 15, 2017), pp. iv43-iv50, XP093248341, ISSN: 1462-0324, DOI: 10.1093/rheumatology/kex419.

Joo Youn Oh, et al., The Link module of human TSG-6 (Link_TSG6) promotes wound healing, suppresses inflammation and improves glandular function in mouse models of Dry Eye Disease, The Ocular Surface (2022), 40-50, 24.

Altschul et al., "Basic Local Alignment Search Tool", J. Mol. Biol., vol. 215, 1990, pp. 403-410.

Baranova et al., "The Inflammation-associated Protein TSG-6 Cross-links Hyaluronan via Hyaluronan-induced TSG-6 Oligomers", The Journal of Biological Chemistry, vol. 286, No. 29, Jul. 22, 2011, pp. 25675-25686.

Blundell et al., "The Link Module from Ovulation- and Inflammation-associated Protein TSG-6 Changes Conformation on Hyaluronan Binding*s", The Journal of Biological Chemistry, vol. 278, No. 49, Dec. 5, 2003, pp. 49261-49270.

Devereux et al., "A comprehensive set of sequence analysis programs for the VAX", Nucleic Acids Research, vol. 12, No. 1, 1984, pp. 387-395.

Dyer et al., "The Anti-inflammatory Protein TSG-6 Regulates Chemokine Function by Inhibiting Chemokine/Glycosaminoglycan Interactions*", The Journal of Biological Chemistry, vol. 291, No. 24, Jun. 10, 2016, pp. 12627-12640.

Dyer et al., "TSG-6 inhibits neutrophil migration via direct interaction with the chemokine CXCL8", J. Immunol., vol. 192, No. 5, Mar. 1, 2014, pp. 2177-2185.

Getting et al., "The Link Module from Human TSG-6 Inhibits Neutrophil Migration in a Hyaluronan- and Inter- -inhibitor-independent Manner*", The Journal of Biological Chemistry, vol. 277, No. 52, Dec. 27, 2002, pp. 51068-51076.

Henikoff et al., "Amino acid substitution matrices from protein blocks", Proc. Natl. Acad. Sci., vol. 89, Nov. 1992, pp. 10915-10919.

Karlin et al., "Applications and statistics for multiple high-scoring segments in molecular sequences", Proc. Natl. Acad. Sci., vol. 90, Jun. 1993, pp. 5873-5877.

Kuznetsova et al., "The N-terminal Module of Thrombospondin-1 Interacts with the Link Domain of TSG-6 and Enhances its Covalent Association with the Heavy Chains of Inter- -trypsin Inhibitor*", The Journal of Biological Chemistry, vol. 280, No. 35, Sep. 2, 2005, pp. 30899-30908.

Mahoney et al., "Characterization of the Interaction between Tumor Necrosis Factor-stimulated Gene-6 and Heparin", The Journal of Biological Chemistry, vol. 280, No. 29, Jul. 22, 2005, pp. 27044-27055.

Mahoney et al., "Mapping the Hyaluronan-binding Site on the Link Module from Human Tumor Necrosis Factor-stimulated Gene-6 by Site-directed Mutagenesis", The Journal of Biological Chemistry, vol. 276, No. 25, Jun. 22, 2001, pp. 22764-22771.

Mahoney et al., "TSG-6 Regulates Bone Remodeling through Inhibition of Osteoblastogenesis and Osteoclast Activations", The Journal of Biological Chemistry vol. 283, No. 38, Sep. 19, 2008, pp. 25952-25962.

Nentwich et al., "A Novel Allelic Variant of the Human TSG-6 Gene Encoding an Amino Acid Difference in the CUB Module", The Journal of Biological Chemistry, vol. 277, No. 18, May 3, 2002, pp. 15354-15362.

Parkar et al., "Overlapping sites on the Link module of human TSG-6 mediate binding to hyaluronan and chondroitin-4-sulphate", FEBS Letters, vol. 410, No. 2-3, Jun. 30, 1997, pp. 413-417.

Parkar et al., "TSG-6 interacts with hyaluronan and aggrecan in a pH-dependent manner via a common functional element: implications for its regulation in infamed cartilage", FEBS Letters, vol. 428, 1998, pp. 171-176.

Salustri et al., "PTX3 plays a key role in the organization of the cumulus oophrus extracellular matrix and in in vivo fertilization", Development, vol. 131, No. 9, 2004, pp. 1577-1586.

Stephen F. Altschul, "A Protein Alignment Scoring System Sensitive at All Evolutionary Distances", J. Mol. Evol., vol. 36, 1993, pp. 290-300.

Akpek EK, Sheppard JD, Krösser S. Corneal Staining Responder Analysis: A Clinically Meaningful Dry Eye Outcome. Ophthalmology. Dec. 2025; 132(12):1335-1341. doi: 10.1016/j.ophtha.2025.07.015. Epub Jul. 24, 2025. PMID: 40714162.

Aragona P, et al. Modern approach to the treatment of dry eye, a complex multifactorial disease: a P.I.C.A.S.S.O. board review. Br J Ophthalmol. Apr. 2021;105(4):446-453. doi: 10.1136/bjophthalmol-2019-315747. Epub Jul. 23, 2020. PMID: 32703782; PMCID: PMC8005804.

Oh, J.Y. et al., "Anti-inflammatory protein TSG-6 reduces inflammatory damage to the cornea following chemical and mechanical injury," PNAS, vol. 107; No. 39; 16875-16880 (2010).

Sheppard JD, Torkildsen GL, Lonsdale JD, D'Ambrosio FA Jr, McLaurin EB, Eiferman RA, Kennedy KS, Semba CP; OPUS-1 Study Group. Lifitegrast ophthalmic solution 5.0% for treatment of dry eye disease: results of the OPUS-1 phase 3 study. Ophthalmology. Feb. 2014; 121(2):475-83. doi: 10.1016/j.ophtha.2013.09.015. Epub Nov. 26, 2013. PMID: 24289915.

Taloni A, Coco G, Pellegrini M, Scorcia V, Giannaccare G. Efficacy of Perfluorohexyloctane for the Treatment of Patients with Dry Eye Disease: A Meta-Analysis. Ophthalmic Res. 2025;68(1):41-51. doi: 10.1159/000542149. Epub Dec. 2, 2024. PMID: 39622217; PMCID: PMC11844700.

(56) References Cited

OTHER PUBLICATIONS

U.S. Department of Health and Human Services Food and Drug Administration Center for Drug Evaluation and Research (CDER). Dry Eye: Developing Drugs for Treatment—Guidance for Industry (Draft Guidance). Dec. 2020.

Curtis (Osteoarthritis Symptoms and Signs, Nov. 12, 2020) (Year: 2020).

Non-Final Office Action received for U.S. Appl. No. 18/262,113, mailed on Jan. 16, 2026, 23 pages.

Final Office Action received for U.S. Appl. No. 18/262,113, mailed on May 6, 2026, 22 pages.

* cited by examiner

| SEQ ID NO | Description | Sequence | |
|---|---|---|---|
| 1 | Nucleic acid sequence encoding the full-length Q144 allotypic variant of human TSG-6. | cagtcacatt tcagccactg ctctgagaat ttgtgagcag cccctaacag gctgttactt | 60 |
| | | cactacaact gacgat atg atc atc tta att tac tta ttt ctc ttg cta tgg<br>               Met Ile Ile Leu Ile Tyr Leu Phe Leu Leu Leu Trp<br>               1         5             10 | 112 |
| | | gaa gac act caa gga tgg gga ttc aag gat gga att ttt cat aac tcc<br>Glu Asp Thr Gln Gly Trp Gly Phe Lys Asp Gly Ile Phe His Asn Ser<br>     15          20          25 | 160 |
| | | ata tgg ctt gaa cga gca gcc ggt gtg tac cac aga gaa gca cgg tct<br>Ile Trp Leu Glu Arg Ala Ala Gly Val Tyr His Arg Glu Ala Arg Ser<br>     30          35          40 | 208 |
| | | ggc aaa tac aag ctc acc tac gca gaa gct aag gcg gtg tgt gaa ttt<br>Gly Lys Tyr Lys Leu Thr Tyr Ala Glu Ala Lys Ala Val Cys Glu Phe<br>45          50          55          60 | 256 |
| | | gaa ggc ggc cat ctc gca act tac aag cag cta gag gca gcc aga aaa<br>Glu Gly Gly His Leu Ala Thr Tyr Lys Gln Leu Glu Ala Ala Arg Lys<br>          65          70          75 | 304 |
| | | att gga ttt cat gtc tgt gct gct gga tgg atg gct aag ggc aga gtt<br>Ile Gly Phe His Val Cys Ala Ala Gly Trp Met Ala Lys Gly Arg Val<br>          80          85          90 | 352 |
| | | gga tac ccc att gtg aag cca ggg ccc aac tgt gga ttt gga aaa act<br>Gly Tyr Pro Ile Val Lys Pro Gly Pro Asn Cys Gly Phe Gly Lys Thr<br>          95          100        105 | 400 |
| | | ggc att att gat tat gga atc cgt ctc aat agg agt gaa aga tgg gat<br>Gly Ile Ile Asp Tyr Gly Ile Arg Leu Asn Arg Ser Glu Arg Trp Asp<br>          110        115        120 | 448 |
| | | gcc tat tgc tac aac cca cac gca aag gag tgt ggt ggc gtc ttt aca<br>Ala Tyr Cys Tyr Asn Pro His Ala Lys Glu Cys Gly Gly Val Phe Thr<br>125         130          135        140 | 496 |
| | | gat cca aag caa att ttt aaa tct cca ggc ttc cca aat gag tac gaa<br>Asp Pro Lys Gln Ile Phe Lys Ser Pro Gly Phe Pro Asn Glu Tyr Glu<br>          145        150        155 | 544 |
| | | gat aac caa atc tgc tac tgg cac att aga ctc aag tat ggt cag cgt<br>Asp Asn Gln Ile Cys Tyr Trp His Ile Arg Leu Lys Tyr Gly Gln Arg<br>          160        165        170 | 592 |
| | | att cac ctg agt ttt tta gat ttt gac ctt gaa gat gac cca ggt tgc<br>Ile His Leu Ser Phe Leu Asp Phe Asp Leu Glu Asp Asp Pro Gly Cys<br>          175        180        185 | 640 |
| | | ttg gct gat tat gtt gaa ata tat gac agt tac gat gat gtc cat ggc<br>Leu Ala Asp Tyr Val Glu Ile Tyr Asp Ser Tyr Asp Asp Val His Gly<br>          190        195        200 | 688 |
| | | ttt gtg gga aga tac tgt gga gat gag ctt cca gat gac atc atc agt<br>Phe Val Gly Arg Tyr Cys Gly Asp Glu Leu Pro Asp Asp Ile Ile Ser<br>205         210          215        220 | 736 |
| | | aca gga aat gtc atg acc ttg aag ttt cta agt gat gct tca gtg aca<br>Thr Gly Asn Val Met Thr Leu Lys Phe Leu Ser Asp Ala Ser Val Thr<br>          225        230        235 | 784 |
| | | gct gga ggt ttc caa atc aaa tat gtt gca atg gat cct gta tcc aaa<br>Ala Gly Gly Phe Gln Ile Lys Tyr Val Ala Met Asp Pro Val Ser Lys<br>          240        245        250 | 832 |
| | | tcc agt caa gga aaa aat aca agt act act tct act gga aat aaa aac<br>Ser Ser Gln Gly Lys Asn Thr Ser Thr Thr Ser Thr Gly Asn Lys Asn<br>          255        260        265 | 880 |
| | | ttt tta gct gga aga ttt agc cac tta taa aaaaaaaaaa aaggatgatc | 930 |

*FIG. 1A*

| | | | |
|---|---|---|---|
| | | Phe Leu Ala Gly Arg Phe Ser His Leu<br>   270               275 | |
| | | aaaacacaca gtgtttatgt tggaatcttt tggaactcct ttgatctcac tgttattatt | 990 |
| | | aacatttatt tattattttt ctaaatgtga aagcaataca taatttaggg aaaattggaa | 1050 |
| | | aatataggaa actttaaacg agaaaatgaa acctctcata atcccactgc atagaaataa | 1110 |
| | | caagcgttaa cattttcata tttttttctt tcagtcattt ttctatttgt ggtatatgta | 1170 |
| | | tatatgtacc tatatgtatt tgcatttgaa attttggaat cctgctctat gtacagtttt | 1230 |
| | | gtattatact tttaaatct tgaactttat aaacattttc tgaaatcatt gattattcta | 1290 |
| | | caaaaacatg attttaaaca gctgtaaaat attctatgat atgaatgttt tatgcattat | 1350 |
| | | ttaagcctgt ctctattgtt ggaatttcag gtcattttca taaatattgt tgcaataaat | 1410 |
| | | atccttgaac acaaaaaaaa aaaaaaaaaa | 1440 |
| 2 | Amino acid sequence of full-length Q144 allotypic variant of human TSG-6. This allotypic variant has a glutamine residue (Q) at position 144. It is the most common allotypic variant and is found in approximately 86% of the Caucasian population (Nentwich et al. (2002) 277, 15354-15362). | Met Ile Ile Leu Ile Tyr Leu Phe Leu Leu Leu Trp Glu Asp Thr Gln<br>1          5            10          15<br><br>Gly Trp Gly Phe Lys Asp Gly Ile Phe His Asn Ser Ile Trp Leu Glu<br>      20          25          30<br><br>Arg Ala Ala Gly Val Tyr His Arg Glu Ala Arg Ser Gly Lys Tyr Lys<br>      35          40          45<br><br>Leu Thr Tyr Ala Glu Ala Lys Ala Val Cys Glu Phe Glu Gly Gly His<br>      50          55          60<br><br>Leu Ala Thr Tyr Lys Gln Leu Glu Ala Ala Arg Lys Ile Gly Phe His<br>65          70          75          80<br><br>Val Cys Ala Ala Gly Trp Met Ala Lys Gly Arg Val Gly Tyr Pro Ile<br>          85          90          95<br><br>Val Lys Pro Gly Pro Asn Cys Gly Phe Gly Lys Thr Gly Ile Ile Asp<br>          100        105        110<br><br>Tyr Gly Ile Arg Leu Asn Arg Ser Glu Arg Trp Asp Ala Tyr Cys Tyr<br>          115        120        125<br><br>Asn Pro His Ala Lys Glu Cys Gly Gly Val Phe Thr Asp Pro Lys Gln<br>          130        135        140<br><br>Ile Phe Lys Ser Pro Gly Phe Pro Asn Glu Tyr Glu Asp Asn Gln Ile<br>145        150        155       160<br><br>Cys Tyr Trp His Ile Arg Leu Lys Tyr Gly Gln Arg Ile His Leu Ser<br>          165        170        175<br><br>Phe Leu Asp Phe Asp Leu Glu Asp Asp Pro Gly Cys Leu Ala Asp Tyr<br>          180        185        190<br><br>Val Glu Ile Tyr Asp Ser Tyr Asp Asp Val His Gly Phe Val Gly Arg<br>          195        200        205<br><br>Tyr Cys Gly Asp Glu Leu Pro Asp Asp Ile Ile Ser Thr Gly Asn Val<br>          210        215        220<br><br>Met Thr Leu Lys Phe Leu Ser Asp Ala Ser Val Thr Ala Gly Gly Phe<br>225        230        235       240<br><br>Gln Ile Lys Tyr Val Ala Met Asp Pro Val Ser Lys Ser Ser Gln Gly<br>          245        250        255<br><br>Lys Asn Thr Ser Thr Thr Ser Thr Gly Asn Lys Asn Phe Leu Ala Gly<br>          260        265        270<br><br>Arg Phe Ser His Leu<br>      275 | |

FIG. 1B

| 3 | The amino acid sequence of the Q144 allotypic variant of human TSG-6 without the signal sequence (corresponds to residues 18-277 of SEQ ID NO: 2). | Trp Gly Phe Lys Asp Gly Ile Phe His Asn Ser Ile Trp Leu Glu Arg<br>1             5                 10            15<br><br>Ala Ala Gly Val Tyr His Arg Glu Ala Arg Ser Gly Lys Tyr Lys Leu<br>        20              25              30<br><br>Thr Tyr Ala Glu Ala Lys Ala Val Cys Glu Phe Glu Gly Gly His Leu<br>      35              40             45<br><br>Ala Thr Tyr Lys Gln Leu Glu Ala Ala Arg Lys Ile Gly Phe His Val<br>      50              55              60<br><br>Cys Ala Ala Gly Trp Met Ala Lys Gly Arg Val Gly Tyr Pro Ile Val<br>65             70              75            80<br><br>Lys Pro Gly Pro Asn Cys Gly Phe Gly Lys Thr Gly Ile Ile Asp Tyr<br>          85              90              95<br><br>Gly Ile Arg Leu Asn Arg Ser Glu Arg Trp Asp Ala Tyr Cys Tyr Asn<br>         100             105           110<br><br>Pro His Ala Lys Glu Cys Gly Gly Val Phe Thr Asp Pro Lys Gln Ile<br>        115            120           125<br><br>Phe Lys Ser Pro Gly Phe Pro Asn Glu Tyr Glu Asp Asn Gln Ile Cys<br>      130            135             140<br><br>Tyr Trp His Ile Arg Leu Lys Tyr Gly Gln Arg Ile His Leu Ser Phe<br>145             150           155           160<br><br>Leu Asp Phe Asp Leu Glu Asp Asp Pro Gly Cys Leu Ala Asp Tyr Val<br>         165            170           175<br><br>Glu Ile Tyr Asp Ser Tyr Asp Asp Val His Gly Phe Val Gly Arg Tyr<br>        180            185           190<br><br>Cys Gly Asp Glu Leu Pro Asp Asp Ile Ile Ser Thr Gly Asn Val Met<br>        195            200          205<br><br>Thr Leu Lys Phe Leu Ser Asp Ala Ser Val Thr Ala Gly Gly Phe Gln<br>      210            215          220<br><br>Ile Lys Tyr Val Ala Met Asp Pro Val Ser Lys Ser Ser Gln Gly Lys<br>225             230           235          240<br><br>Asn Thr Ser Thr Thr Ser Thr Gly Asn Lys Asn Phe Leu Ala Gly Arg<br>         245             250          255<br><br>Phe Ser His Leu<br>      260 |
| 4 | The nucleic acid sequence encoding the full-length R144 allotypic variant of human TSG-6. | cagtcacatt tcagccactg ctctgagaat ttgtgagcag cccctaacag gctgttactt    60<br><br>cactacaact gacgat atg atc atc tta att tac tta ttt ctc ttg cta tgg    112<br>                     Met Ile Ile Leu Ile Tyr Leu Phe Leu Leu Leu Trp<br>                     1           5             10<br><br>gaa gac act caa gga tgg gga ttc aag gat gga att ttt cat aac tcc    160<br>Glu Asp Thr Gln Gly Trp Gly Phe Lys Asp Gly Ile Phe His Asn Ser<br>         15             20           25<br><br>ata tgg ctt gaa cga gca gcc ggt gtg tac cac aga gaa gca cgg tct    208<br>Ile Trp Leu Glu Arg Ala Ala Gly Val Tyr His Arg Glu Ala Arg Ser<br>         30             35           40<br><br>ggc aaa tac aag ctc acc tac gca gaa gct aag gcg gtg tgt gaa ttt    256<br>Gly Lys Tyr Lys Leu Thr Tyr Ala Glu Ala Lys Ala Val Cys Glu Phe<br>45             50           55          60<br><br>gaa ggc ggc cat ctc gca act tac aag cag cta gag gca gcc aga aaa    304<br>Glu Gly Gly His Leu Ala Thr Tyr Lys Gln Leu Glu Ala Ala Arg Lys<br>         65             70           75<br><br>att gga ttt cat gtc tgt gct gct gga tgg atg gct aag ggc aga gtt    352<br>Ile Gly Phe His Val Cys Ala Ala Gly Trp Met Ala Lys Gly Arg Val<br>         80             85           90 |

_FIG. 1C_

|  |  |  |  |
|---|---|---|---|
| | gga tac ccc att gtg aag cca ggg ccc aac tgt gga ttt gga aaa act | 400 |
| | Gly Tyr Pro Ile Val Lys Pro Gly Pro Asn Cys Gly Phe Gly Lys Thr | |
| | 95 100 105 | |
| | ggc att att gat tat gga atc cgt ctc aat agg agt gaa aga tgg gat | 448 |
| | Gly Ile Ile Asp Tyr Gly Ile Arg Leu Asn Arg Ser Glu Arg Trp Asp | |
| | 110 115 120 | |
| | gcc tat tgc tac aac cca cac gca aag gag tgt ggt ggc gtc ttt aca | 496 |
| | Ala Tyr Cys Tyr Asn Pro His Ala Lys Glu Cys Gly Gly Val Phe Thr | |
| | 125 130 135 140 | |
| | gat cca aag cgg att ttt aaa tct cca ggc ttc cca aat gag tac gaa | 544 |
| | Asp Pro Lys Arg Ile Phe Lys Ser Pro Gly Phe Pro Asn Glu Tyr Glu | |
| | 145 150 155 | |
| | gat aac caa atc tgc tac tgg cac att aga ctc aag tat ggt cag cgt | 592 |
| | Asp Asn Gln Ile Cys Tyr Trp His Ile Arg Leu Lys Tyr Gly Gln Arg | |
| | 160 165 170 | |
| | att cac ctg agt ttt tta gat ttt gac ctt gaa gat gac cca ggt tgc | 640 |
| | Ile His Leu Ser Phe Leu Asp Phe Asp Leu Glu Asp Asp Pro Gly Cys | |
| | 175 180 185 | |
| | ttg gct gat tat gtt gaa ata tat gac agt tac gat gat gtc cat ggc | 688 |
| | Leu Ala Asp Tyr Val Glu Ile Tyr Asp Ser Tyr Asp Asp Val His Gly | |
| | 190 195 200 | |
| | ttt gtg gga aga tac tgt gga gat gag ctt cca gat gac atc atc agt | 736 |
| | Phe Val Gly Arg Tyr Cys Gly Asp Glu Leu Pro Asp Asp Ile Ile Ser | |
| | 205 210 215 220 | |
| | aca gga aat gtc atg acc ttg aag ttt cta agt gat gct tca gtg aca | 784 |
| | Thr Gly Asn Val Met Thr Leu Lys Phe Leu Ser Asp Ala Ser Val Thr | |
| | 225 230 235 | |
| | gct gga ggt ttc caa atc aaa tat gtt gca atg gat cct gta tcc aaa | 832 |
| | Ala Gly Gly Phe Gln Ile Lys Tyr Val Ala Met Asp Pro Val Ser Lys | |
| | 240 245 250 | |
| | tcc agt caa gga aaa aat aca agt act act tct act gga aat aaa aac | 880 |
| | Ser Ser Gln Gly Lys Asn Thr Ser Thr Thr Ser Thr Gly Asn Lys Asn | |
| | 255 260 265 | |
| | ttt tta gct gga aga ttt agc cac tta taa aaaaaaaaaa aaggatgatc | 930 |
| | Phe Leu Ala Gly Arg Phe Ser His Leu | |
| | 270 275 | |
| | aaaacacaca gtgtttatgt tggaatcttt tggaactcct ttgatctcac tgttattatt | 990 |
| | aacatttatt tattattttt ctaaatgtga aagcaataca taatttaggg aaaattggaa | 1050 |
| | aatataggaa actttaaacg agaaaatgaa acctctcata atcccactgc atagaaataa | 1110 |
| | caagcgttaa cattttcata ttttttcctt tcagtcattt ttctatttgt ggtatatgta | 1170 |
| | tatatgtacc tatatgtatt tgcatttgaa attttggaat cctgctctat gtacagtttt | 1230 |
| | gtattatact ttttaaatct tgaactttat aaacattttc tgaaatcatt gattattcta | 1290 |
| | caaaaacatg attttaaaca gctgtaaaat attctatgat atgaatgttt tatgcattat | 1350 |
| | ttaagcctgt ctctattgtt ggaatttcag gtcattttca taaatattgt tgcaataaat | 1410 |
| | atccttgaac acaaaaaaaa aaaaaaaaaa | 1440 |

| 5 | The amino acid sequence of full-length R144 allotypic variant of human TSG-6. This allotypic variant has an arginine residue (R) at | Met Ile Ile Leu Ile Tyr Leu Phe Leu Leu Leu Trp Glu Asp Thr Gln  1          5                   10                  15  Gly Trp Gly Phe Lys Asp Gly Ile Phe His Asn Ser Ile Trp Leu Glu       20               25                  30  Arg Ala Ala Gly Val Tyr His Arg Glu Ala Arg Ser Gly Lys Tyr Lys       35               40                  45 |  |

*FIG. 1D*

|   | position 144. It is the less common allotypic variant and is found in approximately 14% of the Caucasian population (Nentwich et al. (2002) 277, 15354-15362). | Leu Thr Tyr Ala Glu Ala Lys Ala Val Cys Glu Phe Glu Gly Gly His<br>    50           55           60<br>Leu Ala Thr Tyr Lys Gln Leu Glu Ala Ala Arg Lys Ile Gly Phe His<br>65          70           75        80<br>Val Cys Ala Ala Gly Trp Met Ala Lys Gly Arg Val Gly Tyr Pro Ile<br>        85          90          95<br>Val Lys Pro Gly Pro Asn Cys Gly Phe Gly Lys Thr Gly Ile Ile Asp<br>        100        105        110<br>Tyr Gly Ile Arg Leu Asn Arg Ser Glu Arg Trp Asp Ala Tyr Cys Tyr<br>        115        120        125<br>Asn Pro His Ala Lys Glu Cys Gly Gly Val Phe Thr Asp Pro Lys Arg<br>        130        135        140<br>Ile Phe Lys Ser Pro Gly Phe Pro Asn Glu Tyr Glu Asp Asn Gln Ile<br>145          150         155      160<br>Cys Tyr Trp His Ile Arg Leu Lys Tyr Gly Gln Arg Ile His Leu Ser<br>        165        170        175<br>Phe Leu Asp Phe Asp Leu Glu Asp Asp Pro Gly Cys Leu Ala Asp Tyr<br>        180        185        190<br>Val Glu Ile Tyr Asp Ser Tyr Asp Asp Val His Gly Phe Val Gly Arg<br>        195        200        205<br>Tyr Cys Gly Asp Glu Leu Pro Asp Asp Ile Ile Ser Thr Gly Asn Val<br>        210        215        220<br>Met Thr Leu Lys Phe Leu Ser Asp Ala Ser Val Thr Ala Gly Gly Phe<br>225          230         235      240<br>Gln Ile Lys Tyr Val Ala Met Asp Pro Val Ser Lys Ser Ser Gln Gly<br>        245        250        255<br>Lys Asn Thr Ser Thr Thr Ser Thr Gly Asn Lys Asn Phe Leu Ala Gly<br>        260        265        270<br>Arg Phe Ser His Leu<br>275 |
| 6 | The amino acid sequence of the R144 allotypic variant of human TSG-6 without the signal sequence (corresponds to residues 18-277 of SEQ ID NO: 5). | Trp Gly Phe Lys Asp Gly Ile Phe His Asn Ser Ile Trp Leu Glu Arg<br>1          5           10        15<br>Ala Ala Gly Val Tyr His Arg Glu Ala Arg Ser Gly Lys Tyr Lys Leu<br>        20        25        30<br>Thr Tyr Ala Glu Ala Lys Ala Val Cys Glu Phe Glu Gly Gly His Leu<br>        35        40        45<br>Ala Thr Tyr Lys Gln Leu Glu Ala Ala Arg Lys Ile Gly Phe His Val<br>        50        55        60<br>Cys Ala Ala Gly Trp Met Ala Lys Gly Arg Val Gly Tyr Pro Ile Val<br>65          70         75        80<br>Lys Pro Gly Pro Asn Cys Gly Phe Gly Lys Thr Gly Ile Ile Asp Tyr<br>        85        90        95<br>Gly Ile Arg Leu Asn Arg Ser Glu Arg Trp Asp Ala Tyr Cys Tyr Asn<br>        100        105        110<br>Pro His Ala Lys Glu Cys Gly Gly Val Phe Thr Asp Pro Lys Arg Ile<br>        115        120        125<br>Phe Lys Ser Pro Gly Phe Pro Asn Glu Tyr Glu Asp Asn Gln Ile Cys<br>        130        135        140<br>Tyr Trp His Ile Arg Leu Lys Tyr Gly Gln Arg Ile His Leu Ser Phe<br>145          150         155      160<br>Leu Asp Phe Asp Leu Glu Asp Asp Pro Gly Cys Leu Ala Asp Tyr Val |

FIG. 1E

| | | | |
|---|---|---|---|
| | |        165           170           175<br><br>Glu Ile Tyr Asp Ser Tyr Asp Asp Val His Gly Phe Val Gly Arg Tyr<br>         180           185         190<br><br>Cys Gly Asp Glu Leu Pro Asp Asp Ile Ile Ser Thr Gly Asn Val Met<br>         195           200         205<br><br>Thr Leu Lys Phe Leu Ser Asp Ala Ser Val Thr Ala Gly Gly Phe Gln<br>     210           215         220<br><br>Ile Lys Tyr Val Ala Met Asp Pro Val Ser Lys Ser Ser Gln Gly Lys<br>225          230          235         240<br><br>Asn Thr Ser Thr Thr Ser Thr Gly Asn Lys Asn Phe Leu Ala Gly Arg<br>         245           250         255<br><br>Phe Ser His Leu<br>         260 | |
| 7 | The amino acid sequence of the Link module of human TSG-6 (corresponds to residues 37-128 of SEQ ID NOs: 2 and 5). | Val Tyr His Arg Glu Ala Arg Ser Gly Lys Tyr Lys Leu Thr Tyr Ala<br>1         5           10         15<br><br>Glu Ala Lys Ala Val Cys Glu Phe Glu Gly Gly His Leu Ala Thr Tyr<br>         20           25         30<br><br>Lys Gln Leu Glu Ala Ala Arg Lys Ile Gly Phe His Val Cys Ala Ala<br>         35           40         45<br><br>Gly Trp Met Ala Lys Gly Arg Val Gly Tyr Pro Ile Val Lys Pro Gly<br>         50           55         60<br><br>Pro Asn Cys Gly Phe Gly Lys Thr Gly Ile Ile Asp Tyr Gly Ile Arg<br>65         70           75         80<br><br>Leu Asn Arg Ser Glu Arg Trp Asp Ala Tyr Cys Tyr<br>         85           90 | |
| 8 | Nucleic acid sequence encoding Link_TSG6 used in the Examples (Day *et al.* (1996) *Protein Expr. Pruif.* 8, 1-16). | aggagatata cat atg ggt gtg tac cac cgt gaa gca cgg tct ggc aaa<br>               Met Gly Val Tyr His Arg Glu Ala Arg Ser Gly Lys<br>               1         5           10<br><br>tac aag ctc acc tac gca gaa gct aag gcg gtg tgt gaa ttt gaa ggc<br>Tyr Lys Leu Thr Tyr Ala Glu Ala Lys Ala Val Cys Glu Phe Glu Gly<br>         15           20         25<br><br>ggc cat ctc gca act tac aag cag cta gag gca gcc cgt aaa att gga<br>Gly His Leu Ala Thr Tyr Lys Gln Leu Glu Ala Ala Arg Lys Ile Gly<br>         30           35         40<br><br>ttt cat gtc tgt gct gct gga tgg atg gct aag ggc cgt gtt gga tac<br>Phe His Val Cys Ala Ala Gly Trp Met Ala Lys Gly Arg Val Gly Tyr<br>45         50           55         60<br><br>ccc att gtg aag cca ggg ccc aac tgt gga ttt gga aaa act ggc att<br>Pro Ile Val Lys Pro Gly Pro Asn Cys Gly Phe Gly Lys Thr Gly Ile<br>               65           70         75<br><br>att gat tat gga atc cgt ctc aat agg agt gaa cgt tgg gat gcc tat<br>Ile Asp Tyr Gly Ile Arg Leu Asn Arg Ser Glu Arg Trp Asp Ala Tyr<br>         80           85         90<br><br>tgc tac aac cca cac gca aag taa gaattc<br>Cys Tyr Asn Pro His Ala Lys<br>         95 | 49<br><br><br>97<br><br><br>145<br><br><br>193<br><br><br>241<br><br><br>289<br><br><br>319 |
| 9 | The amino acid sequence of Link_TSG6 used in the Examples. Residues 2-93 of SEQ ID NO: 9 correspond | Gly Val Tyr His Arg Glu Ala Arg Ser Gly Lys Tyr Lys Leu Thr<br><br>Tyr Ala Glu Ala Lys Ala Val Cys Glu Phe Glu Gly Gly His Leu Ala<br><br>Thr Tyr Lys Gln Leu Glu Ala Ala Arg Lys Ile Gly Phe His Val Cys<br><br>Ala Ala Gly Trp Met Ala Lys Gly Arg Val Gly Tyr Pro Ile Val Lys<br><br>Pro Gly Pro Asn Cys Gly Phe Gly Lys Thr Gly Ile Ile Asp Tyr Gly<br><br>Ile Arg Leu Asn Arg Ser Glu Arg Trp Asp Ala Tyr Cys Tyr Asn Pro | |

*FIG. 1F*

| | to SEQ ID NO: 7 (residues 37-128 of SEQ ID NOs: 2 and 5). | His Ala Lys |
|---|---|---|

FIG. 1G

Ocular staining

Tear production

Conjunctival goblet cell

Conjunctival goblet cell

Inflammatory foci
(Intraorbital gland)

Pre-treatment

Post-treatment

Goblet cell count

MMP-9
(Ocular surface)

SEQUENCE LISTING

```
<160> NUMBER OF SEQ ID NOS: 9

<210> SEQ ID NO 1
<211> LENGTH: 1440
<212> TYPE: DNA
<213> ORGANISM: Artificial Sequence
<220> FEATURE:
<223> OTHER INFORMATION: Nucleic acid sequence encoding the full-length
      Q144 allotypic variant of human TSG-6

<400> SEQUENCE: 1
cagtcacatt tcagccactg ctctgagaat ttgtgagcag cccctaacag gctgttactt        60
cactacaact gacgatatga tcatcttaat ttacttattt ctcttgctat gggaagacac       120
tcaaggatgg ggattcaagg atggaatttt tcataactcc atatggcttg aacgagcagc       180
cggtgtgtac cacagagaag cacggtctgg caaatacaag ctcacctacg cagaagctaa       240
ggcggtgtgt gaatttgaag gcggccatct cgcaacttac aagcagctag aggcagccag       300
aaaaattgga tttcatgtct gtgctgctgg atggatggct aagggcagag ttggataccc       360
cattgtgaag ccagggccca actgtggatt tggaaaaact ggcattattg attatggaat       420
ccgtctcaat aggagtgaaa gatgggatgc ctattgctac aacccacacg caaaggagtg       480
tggtggcgtc tttacagatc caaagcaaat ttttaaatct ccaggcttcc caaatgagta       540
cgaagataac caaatctgct actggcacat tagactcaag tatggtcagc gtattcacct       600 gagttttta gattttgacc ttgaagatga cccaggttgc ttggctgatt atgttgaaat       660
atatgacagt tacgatgatg tccatggctt tgtgggaaga tactgtggag atgagcttcc       720
```

-continued

```
agatgacatc atcagtacag gaaatgtcat gaccttgaag tttctaagtg atgcttcagt       780
gacagctgga ggtttccaaa tcaaatatgt tgcaatggat cctgtatcca aatccagtca       840
aggaaaaaat acaagtacta cttctactgg aaataaaaac tttttagctg gaagatttag       900
ccacttataa aaaaaaaaaa aaggatgatc aaaacacaca gtgtttatgt tggaatcttt       960
tggaactcct ttgatctcac tgttattatt aacatttatt tattatttt ctaaatgtga      1020 aagcaataca taatttaggg aaaattggaa aatataggaa actttaaacg agaaatgaa      1080 acctctcata atcccactgc atagaaataa caagcgttaa cattttcata ttttttctt      1140 tcagtcattt ttctatttgt ggtatatgta tatgtacc tatatgtatt tgcatttgaa      1200
attttggaat cctgctctat gtacagtttt gtattatact ttttaaatct tgaactttat      1260
aaacattttc tgaaatcatt gattattcta caaaaacatg attttaaaca gctgtaaaat      1320
attctatgat atgaatgttt tatgcattat ttaagcctgt ctctattgtt ggaatttcag      1380
gtcattttca taaatattgt tgcaataaat atccttgaac acaaaaaaaa aaaaaaaaaa      1440
```

<210> SEQ ID NO 2
<211> LENGTH: 277
<212> TYPE: PRT
<213> ORGANISM: Artificial Sequence
<220> FEATURE:
<223> OTHER INFORMATION: Amino acid sequence of full-length Q144
      allotypic variant of human TSG-6

<400> SEQUENCE: 2

```
Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
            115                 120                 125

Asn Pro His Ala Lys Glu Cys Gly Gly Val Phe Thr Asp Pro Lys Gln
        130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
            195                 200                 205

Tyr Cys Gly Asp Glu Leu Pro Asp Asp Ile Ile Ser Thr Gly Asn Val
        210                 215                 220

Met Thr Leu Lys Phe Leu Ser Asp Ala Ser Val Thr Ala Gly Gly Phe
225                 230                 235                 240
```

-continued

```
Gln Ile Lys Tyr Val Ala Met Asp Pro Val Ser Lys Ser Ser Gln Gly
            245                 250                 255

Lys Asn Thr Ser Thr Thr Ser Thr Gly Asn Lys Asn Phe Leu Ala Gly
            260                 265                 270

Arg Phe Ser His Leu
        275

<210> SEQ ID NO 3
<211> LENGTH: 260
<212> TYPE: PRT
<213> ORGANISM: Artificial Sequence
<220> FEATURE:
<223> OTHER INFORMATION: The amino acid sequence of the Q144 allotypic
      variant of human TSG-6 without the signal sequence

<400> SEQUENCE: 3

Trp Gly Phe Lys Asp Gly Ile Phe His Asn Ser Ile Trp Leu Glu Arg
1               5                   10                  15

Ala Ala Gly Val Tyr His Arg Glu Ala Arg Ser Gly Lys Tyr Lys Leu
            20                  25                  30

Thr Tyr Ala Glu Ala Lys Ala Val Cys Glu Phe Glu Gly Gly His Leu
        35                  40                  45

Ala Thr Tyr Lys Gln Leu Glu Ala Ala Arg Lys Ile Gly Phe His Val
    50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
                85                  90                  95

Gly Ile Arg Leu Asn Arg Ser Glu Arg Trp Asp Ala Tyr Cys Tyr Asn
            100                 105                 110

Pro His Ala Lys Glu Cys Gly Gly Val Phe Thr Asp Pro Lys Gln Ile
        115                 120                 125

Phe Lys Ser Pro Gly Phe Pro Asn Glu Tyr Glu Asp Asn Gln Ile Cys
    130                 135                 140

Tyr Trp His Ile Arg Leu Lys Tyr Gly Gln Arg Ile His Leu Ser Phe
145                 150                 155                 160

Leu Asp Phe Asp Leu Glu Asp Asp Pro Gly Cys Leu Ala Asp Tyr Val
                165                 170                 175

Glu Ile Tyr Asp Ser Tyr Asp Asp Val His Gly Phe Val Gly Arg Tyr
            180                 185                 190

Cys Gly Asp Glu Leu Pro Asp Asp Ile Ile Ser Thr Gly Asn Val Met
        195                 200                 205

Thr Leu Lys Phe Leu Ser Asp Ala Ser Val Thr Ala Gly Gly Phe Gln
    210                 215                 220

Ile Lys Tyr Val Ala Met Asp Pro Val Ser Lys Ser Ser Gln Gly Lys
225                 230                 235                 240

Asn Thr Ser Thr Thr Ser Thr Gly Asn Lys Asn Phe Leu Ala Gly Arg
                245                 250                 255

Phe Ser His Leu
            260

<210> SEQ ID NO 4
<211> LENGTH: 1440
<212> TYPE: DNA
<213> ORGANISM: Artificial Sequence
<220> FEATURE:
<223> OTHER INFORMATION: The nucleic acid sequence encoding the
```

```
                full-length R144 allotypic variant of human TSG-6

<400> SEQUENCE: 4
cagtcacatt tcagccactg ctctgagaat ttgtgagcag cccctaacag gctgttactt      60
cactacaact gacgatatga tcatcttaat ttacttattt ctcttgctat gggaagacac     120
tcaaggatgg ggattcaagg atggaatttt tcataactcc atatggcttg aacgagcagc     180
cggtgtgtac cacagagaag cacggtctgg caaatacaag ctcacctacg cagaagctaa     240
ggcggtgtgt gaatttgaag gcggccatct cgcaacttac aagcagctag aggcagccag     300
aaaaattgga tttcatgtct gtgctgctgg atggatggct aagggcagag ttggataccc     360
cattgtgaag ccagggccca actgtggatt tggaaaaact ggcattattg attatggaat     420
ccgtctcaat aggagtgaaa gatgggatgc ctattgctac aacccacacg caaaggagtg     480
tggtggcgtc tttacagatc aaagcggat ttttaaatct ccaggcttcc caaatgagta     540
cgaagataac caaatctgct actggcacat tagactcaag tatggtcagc gtattcacct     600 gagttttta gattttgacc ttgaagatga cccaggttgc ttggctgatt atgttgaaat     660
atatgacagt tacgatgatg tccatggctt tgtgggaaga tactgtggag atgagcttcc     720
agatgacatc atcagtacag gaaatgtcat gaccttgaag tttctaagtg atgcttcagt     780
gacagctgga ggtttccaaa tcaaatatgt tgcaatggat cctgtatcca atccagtca     840 aggaaaaaat acaagtacta cttctactgg aaataaaaac tttttagctg gaagatttag     900
ccacttataa aaaaaaaaaa aaggatgatc aaaacacaca gtgtttatgt tggaatcttt     960
tggaactcct ttgatctcac tgttattatt aacatttatt tattattttt ctaaatgtga    1020
aagcaataca taatttaggg aaaattggaa aatataggaa actttaaacg agaaatgaa    1080 acctctcata atcccactgc atagaaataa caagcgttaa cattttcata ttttttttctt    1140 tcagtcattt ttctatttgt ggtatatgta tatatgtacc tatatgtatt tgcatttgaa    1200
attttggaat cctgctctat gtacagtttt gtattatact tttttaaatct tgaacttttat    1260 aaacattttc tgaaatcatt gattattcta caaaaacatg attttaaaca gctgtaaaat    1320
attctatgat atgaatgttt tatgcattat ttaagcctgt ctctattgtt ggaatttcag    1380
gtcattttca taaatattgt tgcaataaat atccttgaac acaaaaaaaa aaaaaaaaaa    1440

<210> SEQ ID NO 5
<211> LENGTH: 277
<212> TYPE: PRT
<213> ORGANISM: Artificial Sequence
<220> FEATURE:
<223> OTHER INFORMATION: The amino acid sequence of full-length R144
      allotypic variant of human TSG-6.

<400> SEQUENCE: 5

Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
                20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
```

-continued

```
                        85               90              95

Val Lys Pro Gly Pro Asn Cys Gly Phe Gly Lys Thr Gly Ile Ile Asp
            100             105             110

Tyr Gly Ile Arg Leu Asn Arg Ser Glu Arg Trp Asp Ala Tyr Cys Tyr
            115             120             125

Asn Pro His Ala Lys Glu Cys Gly Gly Val Phe Thr Asp Pro Lys Arg
        130             135             140

Ile Phe Lys Ser Pro Gly Phe Pro Asn Glu Tyr Glu Asp Asn Gln Ile
145             150             155             160

Cys Tyr Trp His Ile Arg Leu Lys Tyr Gly Gln Arg Ile His Leu Ser
                165             170             175

Phe Leu Asp Phe Asp Leu Glu Asp Asp Pro Gly Cys Leu Ala Asp Tyr
            180             185             190

Val Glu Ile Tyr Asp Ser Tyr Asp Asp Val His Gly Phe Val Gly Arg
            195             200             205

Tyr Cys Gly Asp Glu Leu Pro Asp Asp Ile Ile Ser Thr Gly Asn Val
        210             215             220

Met Thr Leu Lys Phe Leu Ser Asp Ala Ser Val Thr Ala Gly Gly Phe
225             230             235             240

Gln Ile Lys Tyr Val Ala Met Asp Pro Val Ser Lys Ser Ser Gln Gly
                245             250             255

Lys Asn Thr Ser Thr Thr Ser Thr Gly Asn Lys Asn Phe Leu Ala Gly
            260             265             270

Arg Phe Ser His Leu
        275

<210> SEQ ID NO 6
<211> LENGTH: 260
<212> TYPE: PRT
<213> ORGANISM: Artificial Sequence
<220> FEATURE:
<223> OTHER INFORMATION: The amino acid sequence of the R144 allotypic
      variant of human TSG-6 without the signal sequence

<400> SEQUENCE: 6

Trp Gly Phe Lys Asp Gly Ile Phe His Asn Ser Ile Trp Leu Glu Arg
1               5               10              15

Ala Ala Gly Val Tyr His Arg Glu Ala Arg Ser Gly Lys Tyr Lys Leu
            20              25              30

Thr Tyr Ala Glu Ala Lys Ala Val Cys Glu Phe Glu Gly Gly His Leu
        35              40              45

Ala Thr Tyr Lys Gln Leu Glu Ala Ala Arg Lys Ile Gly Phe His Val
        50              55              60

Cys Ala Ala Gly Trp Met Ala Lys Gly Arg Val Gly Tyr Pro Ile Val
65              70              75              80

Lys Pro Gly Pro Asn Cys Gly Phe Gly Lys Thr Gly Ile Ile Asp Tyr
                85              90              95

Gly Ile Arg Leu Asn Arg Ser Glu Arg Trp Asp Ala Tyr Cys Tyr Asn
            100             105             110

Pro His Ala Lys Glu Cys Gly Gly Val Phe Thr Asp Pro Lys Arg Ile
        115             120             125

Phe Lys Ser Pro Gly Phe Pro Asn Glu Tyr Glu Asp Asn Gln Ile Cys
        130             135             140

Tyr Trp His Ile Arg Leu Lys Tyr Gly Gln Arg Ile His Leu Ser Phe
145             150             155             160
```

```
Leu Asp Phe Asp Leu Glu Asp Asp Pro Gly Cys Leu Ala Asp Tyr Val
            165                 170                 175

Glu Ile Tyr Asp Ser Tyr Asp Asp Val His Gly Phe Val Gly Arg Tyr
            180                 185                 190

Cys Gly Asp Glu Leu Pro Asp Asp Ile Ile Ser Thr Gly Asn Val Met
        195                 200                 205

Thr Leu Lys Phe Leu Ser Asp Ala Ser Val Thr Ala Gly Gly Phe Gln
    210                 215                 220

Ile Lys Tyr Val Ala Met Asp Pro Val Ser Lys Ser Ser Gln Gly Lys
225                 230                 235                 240

Asn Thr Ser Thr Thr Ser Thr Gly Asn Lys Asn Phe Leu Ala Gly Arg
            245                 250                 255

Phe Ser His Leu
            260

<210> SEQ ID NO 7
<211> LENGTH: 92
<212> TYPE: PRT
<213> ORGANISM: Artificial Sequence
<220> FEATURE:
<223> OTHER INFORMATION: The amino acid sequence of the Link module of
      human TSG-6

<400> SEQUENCE: 7

Val Tyr His Arg Glu Ala Arg Ser Gly Lys Tyr Lys Leu Thr Tyr Ala
1               5                   10                  15

Glu Ala Lys Ala Val Cys Glu Phe Glu Gly Gly His Leu Ala Thr Tyr
            20                  25                  30

Lys Gln Leu Glu Ala Ala Arg Lys Ile Gly Phe His Val Cys Ala Ala
        35                  40                  45

Gly Trp Met Ala Lys Gly Arg Val Gly Tyr Pro Ile Val Lys Pro Gly
    50                  55                  60

Pro Asn Cys Gly Phe Gly Lys Thr Gly Ile Ile Asp Tyr Gly Ile Arg
65                  70                  75                  80

Leu Asn Arg Ser Glu Arg Trp Asp Ala Tyr Cys Tyr
            85                  90

<210> SEQ ID NO 8
<211> LENGTH: 319
<212> TYPE: DNA
<213> ORGANISM: Artificial Sequence
<220> FEATURE:
<223> OTHER INFORMATION: Nucleic acid sequence encoding Link_TSG6

<400> SEQUENCE: 8
aggagatata catatgggtg tgtaccaccg tgaagcacgg tctggcaaat acaagctcac     60
ctacgcagaa gctaaggcgg tgtgtgaatt tgaaggcggc catctcgcaa cttacaagca    120
gctagaggca gcccgtaaaa ttggatttca tgtctgtgct gctggatgga tggctaaggg    180
ccgtgttgga tacccccattg tgaagccagg gcccaactgt ggatttggaa aaactggcat    240
tattgattat ggaatccgtc tcaataggag tgaacgttgg gatgcctatt gctacaaccc    300
acacgcaaag taagaattc                                                 319

<210> SEQ ID NO 9
<211> LENGTH: 98
<212> TYPE: PRT
<213> ORGANISM: Artificial Sequence
<220> FEATURE:
<223> OTHER INFORMATION: The amino acid sequence of Link_TSG6
```

-continued

```
<400> SEQUENCE: 9

Gly Val Tyr His Arg Glu Ala Arg Ser Gly Lys Tyr Lys Leu Thr Tyr
1               5                   10                  15

Ala Glu Ala Lys Ala Val Cys Glu Phe Glu Gly Gly His Leu Ala Thr
            20                  25                  30

Tyr Lys Gln Leu Glu Ala Ala Arg Lys Ile Gly Phe His Val Cys Ala
        35                  40                  45

Ala Gly Trp Met Ala Lys Gly Arg Val Gly Tyr Pro Ile Val Lys Pro
    50                  55                  60

Gly Pro Asn Cys Gly Phe Gly Lys Thr Gly Ile Ile Asp Tyr Gly Ile
65                  70                  75                  80

Arg Leu Asn Arg Ser Glu Arg Trp Asp Ala Tyr Cys Tyr Asn Pro His
                85                  90                  95

Ala Lys
```

TSG6 POLYPEPTIDE FRAGMENT FOR DRY EYE DISEASE

This application is the U.S. National Stage of International Application No. PCT/EP2020/067448, filed Jun. 23, 2020, which designates the U.S., published in English, and claims priority under 35 U.S.C. § 119 or 365 to Great Britain Application No. GB1910645.9, filed Jul. 25, 2019. The entire teachings of the above applications are incorporated herein by reference.

INCORPORATION BY REFERENCE OF MATERIAL IN ASCII TEXT FILE

This application incorporates by reference the Sequence Listing contained in the following ASCII text file: a) File name: 57391006002_SEQLIST.TXT; created Jan. 21, 2022, 17,000 Bytes in size.

FIELD OF THE INVENTION

The present invention relates to the treatment of ocular surface disorders and particularly, although not exclusively, to the treatment of dry eye disease with a LINK_TSG6 polypeptide.

BACKGROUND

Tumour necrosis factor (TNF)-stimulated gene 6 (TSG-6) is a ~35 kDa secreted product of TNF-stimulated gene-6, expressed in response to inflammatory mediators and growth factors.

While constitutively expressed in a few tissues, TSG-6 is generally upregulated wherever there is inflammation. For the most part TSG-6 exhibits anti-inflammatory and tissue protective properties, but has been implicated as sometimes playing a role in disease pathology, for example, in the lung. While being made by a broad range of cell types, it was the finding that TSG-6 is produced by mesenchymal stem/stromal cells (MSCs) in response to inflammatory signals, and that it mediates many of their immunomodulatory and reparative activities, which has led to a wealth of publications on the therapeutic effects of this intriguing molecule across a wide range of disease models.

TSG-6 is a relatively small protein, with a molecular mass of only ~35-38 kDa, being mainly composed of two modular domains. Given TSG-6's size, it has a surprisingly large number of activities, including the modulation of immune and stromal cell function and its contribution to extracellular matrix formation, mechanics and remodelling. It is the ability of TSG-6 to regulate matrix organization, and to control the association of matrix molecules with cell surface receptors and with extracellular signalling factors (e.g. chemokines), that likely underlies its diverse functional repertoire. In this regard, TSG-6 interacts with a large array of ligands, such as glycosaminoglycans (GAGs), proteoglycan (PG) core proteins and other matrix components, and binds directly to multiple chemokines and bone morphogenetic proteins (BMPs). One particularly unusual function of TSG-6 is its role as an enzyme that catalyses the covalent modification of the non-sulfated GAG hyaluronan (HA) with so-called heavy chains (HCs) from the inter-α-inhibitor (IαI) family of proteoglycans. This process, mediated by the full-length TSG6 protein, but not LINK_TSG6 polypeptides containing only a fragment of TSG-6, results in the formation of HC•HA complexes, and is essential for mammalian ovulation and fertilisation, and also occurs in many other contexts (e.g. inflammation) where HC•HAs either confer tissue protection or contribute to pathological processes.

The sites and contexts of TSG-6 expression, its structure and ligand-binding properties, and how these together underpin its diverse biology and therapeutic potential at a molecular level are reviewed in Day & Milner (Matrix Biology (2019) 78-79, 60-83).

US2015/0057229 describes the use of LINK_TSG6 in inhibiting cartilage degradation.

Dry eye disease (also known as keratoconjunctivitis sicca) is one of the most common ocular diseases, occurring in between 7% and 33% of the population worldwide. It is a multifactorial condition of the tear film and ocular surface and is accompanied by increased osmolarity of the tear film and inflammation of the ocular surface, neurotrophic deficiency and meibomian gland dysfunction.

Kim et al. (2016) (Cornea 35(4), 536-542) compared topically applied TSG-6, cyclosporine and prednisolone for treating dry eye. 12 week old NOD.B10.H2b mice were topically administered with recombinant TSG-6 (0.1%) 4 times a day, 0.05% cyclosporine (RESTASIS® (cyclosporine)) twice a day, or 1% prednisolone (Pred Forte) 4 times a day for 1 week. Topical TSG-6 was found to be as effective in inflammation mediated dry eye as cyclosporine eye drops. However, they conclude that clinical application of TSG-6 is limited by various factors, including difficulty in large-scale production or variation in stability of the recombinant protein.

WO2011/139357 described the use of adult stem cells/progenitor cells and stem cell proteins for the treatment of eye injuries and diseases. They propose therapy based on the discovery that after a chemical burn to the cornea of a rat, application of MSCs or MSC conditioned medium reduced inflammation and revascularisation. They proposed the use of anti-apoptotic and anti-inflammatory proteins such as STC-1 and TSG-6, which are expressed by mesenchymal stem cells. Corneal surface inflammation was created in rat eyes by ethanol application and mechanical debridement of the corneal and limbal epithelium. Application of recombinant full length TSG-6 resulted in reduced corneal opacity and neovascularization as compared to a PBS control, and the authors conclude that proteins produced by MSCs in response to an injury signal can protect the corneal surface from damage by increasing the viability and proliferation of corneal epithelial progenitors and by suppressing inflammation at the corneal surface.

US2016/0075750 (Prockop et al) described a method of producing a protein or polypeptide, such as TSG-6 protein, in mammalian cells suspended in a protein-free medium that includes at least one agent that suppresses production of hyaluronic acid, hyaluronan or a salt thereof.

The present invention has been devised in light of the above considerations.

SUMMARY OF THE INVENTION

The present disclosure relates to LINK_TSG6 polypeptide for use in the treatment or prevention of ocular surface disorder such as dry eye disease or other ocular surface disorders with corneal lesions similar to those observed in dry eye disease. The inventors have found that this polypeptide is capable of reducing or preventing the signs and symptoms of dry eye disease, in a dose-dependent manner. Surprisingly, the inventors have found that this polypeptide is more potent at reducing corneal epithelial defects than full length TSG-6.

In some cases, the treatment or prevention of dry eye disease described herein comprises one or more effects selected from the group consisting: healing of corneal epithelial defects; increase in tear production; suppression of inflammation; and an increase in, or the preservation of, the number of conjunctival goblet cells. Suppression of inflammation may comprise a decrease in the production of one or more pro-inflammatory cytokines in the cornea, the intraorbital lacrimal glands, or both the cornea and the intraorbital lacrimal glands, the pro-inflammatory cytokines optionally selected from TNFα, IFNγ, IL-6 and IL-1β.

The treatment or prevention of dry eye disease may comprise healing of corneal epithelial defects, increase in tear production, suppression of inflammation or an increase in, or the preservation of the number of conjunctival goblet cells as compared to the corneal epithelial defects, tear production, inflammation or number of conjunctival goblet cells prior to the administration of LINK_TSG6 polypeptide, and as compared to administration of PBS vehicle.

The treatment or prevention of dry eye disease may comprise healing of corneal epithelial defects, increase in tear production, suppression of inflammation or an increase in, or the preservation of the number of conjunctival goblet cells as compared to the corneal epithelial defects, tear production, inflammation or number of conjunctival goblet cells in a control individual treated with full-length TSG-6 protein.

In some aspects described herein, the treatment comprises topical administration of LINK_TSG6 polypeptide to the eye. The LINK_TSG6 polypeptide may be formulated as an eye drop. The treatment may comprise the administration of an eye drop comprising LINK_TSG6. The LINK_TSG6 polypeptide may be formulated with, or the treatment may involve co-administration with prednisolone, cyclosporine, XIIDRA® (lifiteqrast), artificial tears, or any combination thereof.

In some aspects, the treatment comprises administering LINK_TSG6 polypeptide two times per day. In some aspects, the treatment comprises administering LINK_TSG6 polypeptide more than two times per day. In some cases, the treatment comprises administering LINK_TSG6 polypeptide fewer than 4 times per day, or fewer than 3 times per day. In some cases, the treatment comprises administering LINK_TSG6 polypeptide once per day. In some cases, the treatment comprises administering LINK_TSG6 polypeptide less frequently than once per day, such as once every two days, one time every three days, once every week, or once every two weeks.

The treatment may involve the administration of between 10-200 µg LINK_TSG6 per eye, such as between 100 and 200 µg LINK_TSG6 per eye, between 100 and 150 µg LINK_TSG6 per eye, between 120 and 150 µg LINK_TSG6 per eye. Preferably, the treatment involves the administration of around 120 µg-150 µg LINK_TSG6 polypeptide per eye, or around 12-15 µg LINK_TSG6 per eye.

The treatment or prevention of ocular surface disorders such as dry eye disease disclosed herein is applicable to dry eye disease associated with any cause. The individual being treated may have a condition that is associated with an increased incidence of dry eye disease, such as Sjögren's syndrome, rheumatoid arthritis or diabetes. In some cases, the individual has Type 1 diabetes or Type 2 diabetes. The individual may be at risk of developing an ocular surface disorder such as dry eye disease due to aging, exposure to air pollution and/or increased use of a visual device (e.g. smart phone, computer, tablet).

The treatment may involve the administration of LINK_TSG6 polypeptide that comprises, consist, or consists essentially of (i) the amino acid sequence of SEQ ID NO: 7 or SEQ ID NO: 9, or (ii) an amino acid sequence having at least 80% identity to the amino acid sequence of SEQ ID NO: 7 or 9.

Also disclosed herein are methods of treatment or prevention of ocular surface disorders such as dry eye disease. The method may involve the administration of a therapeutically effective amount of LINK_TSG6 to a patient in need thereof. It may involve the topical administration of LINK_TSG6 to the eye.

Another aspect disclosed herein is the use of a LINK_TSG6 polypeptide in the manufacture of a medicament for the treatment or prevention of ocular surface disorders such as dry eye disease. The medicament may be formulated for topical administration to the eye, such as an eye drop.

A further aspect disclosed herein is a pharmaceutical composition comprising LINK_TSG6 polypeptide. The pharmaceutical composition may comprise LINK_TSG6 polypeptide solubilised in saline. The pharmaceutical composition may comprise LINK_TSG6 polypeptide solubilised in phosphate buffered saline. In some aspects, the pharmaceutical composition comprises at least 2000 µg/ml, 2100 µg/ml, 2200 µg/ml, 2300 µg/ml 2400 µg/ml, 2500 µg/ml, 2600 µg/ml, 2700 µg/ml, 2800 µg/ml, 2900 µg/ml, 3000 µg/ml, 3100 µg/ml, 3200 µg/ml, 3300 µg/ml or more than 3300 µg/ml LINK_TSG6. In some aspects, the pharmaceutical composition comprises at least 200 µg/ml, 300 µg/ml, 400 µg/ml, 500 µg/ml, 600 µg/ml, 700 µg/ml, 800 µg/ml, 900 µg/ml, 1000 µg/ml, 1200 µg/ml, 1300 µg/ml, 1400 µg/ml, 1500 µg/ml, 1600 µg/ml, 1700 µg/ml, 1800 µg/ml 1900 µg/ml, 2000 µg/ml LINK_TSG6. In some aspects, the pharmaceutical composition comprises at least 200 µg/ml, 300 µg/ml, 400 µg/ml, 500 µg/ml, 600 µg/ml, 700 µg/ml, 800 µg/ml, 900 µg/ml, 1000 µg/ml, 1200 µg/ml, 1300 µg/ml, 1400 µg/ml, 1500 µg/ml, 1600 µg/ml, 1700 µg/ml, 1800 µg/ml 1900 µg/ml, 2000 µg/ml LINK_TSG6. Preferably, the pharmaceutical formation comprises at least 2000 µg/ml LINK_TSG6. Such formulations are useful for delivering between around 120 µg and around 150 µg of LINK_TSG6 per drop.

The pharmaceutical composition may be an eye drop formulation. The eye drop formulation may comprise between 1500 µg/ml and 3500 µg/ml, between 1500 µg/ml and 3000 µg/ml, between 2000 µg/ml and 3000 µg/ml, or between 2400 µg/ml and 3000 µg/ml. Preferably, the eye drop formulation comprises between about 2400 µg/ml and about 3000 µg/ml. In some cases, the eye drop formulation comprises at least 2200, at least 2300 µg/ml, at least 2400 µg/ml, at least 2500 µg/ml, at least 2600 µg/ml, at least 2700 µg/ml, at least 2800 µg/ml, at least 2900 µg/ml, at least 3000 µg/ml or more than 3000 µg/ml. The eye drop formulation may further comprise prednisolone, cyclosporine, XIIDRA® (lifitegrast) or artificial tears. The eye drop formulation may comprise a pharmaceutically acceptable carrier. The eye drop formulation may comprise LINK_TSG6 polypeptide solubilised in saline. The eye drop formulation may comprise LINK_TSG6 polypeptide solubilised in phosphate buffered saline.

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which:

Figure 1G:
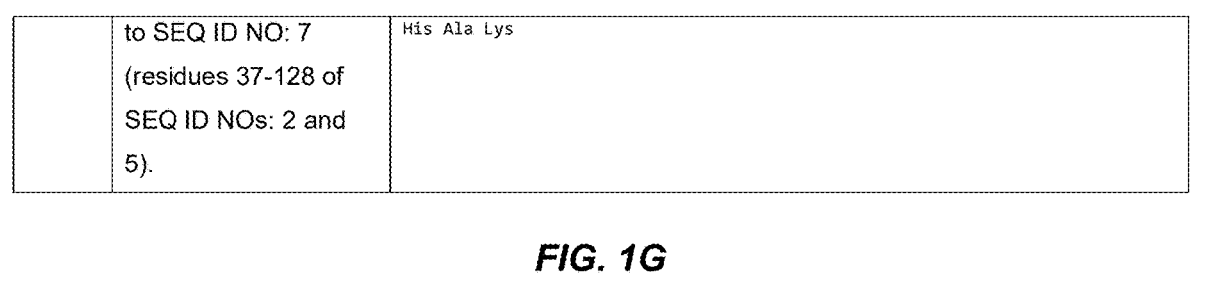

FIGS. 1A-1G. Sequences relevant to the present disclosure.

DETAILED DESCRIPTION OF THE INVENTION

Figure 2A:
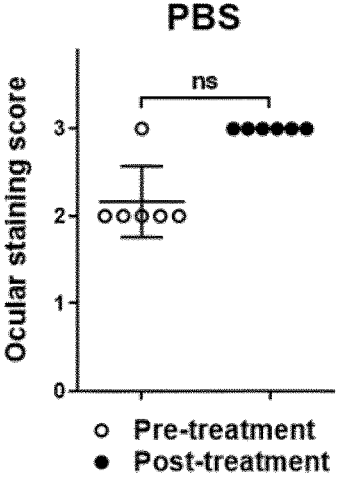
FIG. 2. LINK_TSG6 reduces the signs of dry eye disease. A. Ocular staining score following lissamine green staining; B. Aqueous tear production as determined by phenol red thread test; C. Pro-inflammatory cytokine mRNA level as determined by real-time RT-PCR; D. Conjunctival goblet cell counts in PAS (Periodic acid-Schiff stain) stained conjunctival sections. For A and B significance was determined by Wilcoxon matched-pairs signed rank test for comparison between pre- and post-treatment and Mann-Whitney U test for comparison between PBS and LINK_TSG6. ns=not significant, p>0.05; =p<0.01; *=p<0.001. For C and D significance was determined by one-way ANOVA and Tukey's multiple comparisons test. ns=not significant, p>0.05; *=p<0.05; =p<0.01; *=p<0.001; ****=p<0.0001.
Figure 2A:
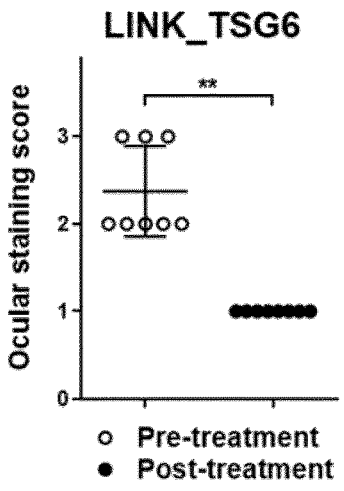
Figure 2A:
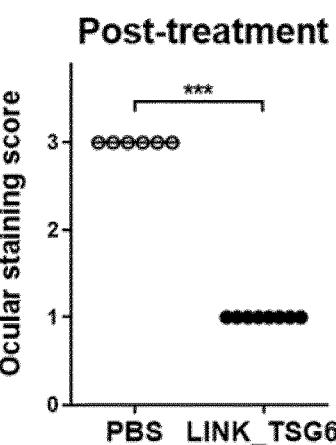

Aspects and embodiments of the present invention will now be discussed with reference to the accompanying figures. Further aspects and embodiments will be apparent to those skilled in the art. All documents mentioned in this text are incorporated herein by reference.

The present invention provides a method for treating or preventing ocular surface disorders such as dry eye disease, which method comprises administering to a subject a LINK_TSG6 polypeptide. The inventors have shown that LINK_TSG6 is more potent than recombinant human TSG-6 in reducing corneal epithelial lesions and treating or reducing the signs or symptoms of ocular surface disorders such as dry eye disease. Without wishing to be bound by theory, this may be a result of improved penetration into the tissue (due to the smaller size of the molecule), differences in the biodistribution as compared to the full length protein, or the absence of signalling or enzymatic activities effected by the CUB_C domain. In this regard, full length TSG-6 binds more effectively to HA than LINK_TSG6 since the former interaction is cooperative (and likely involves CUB_C domain) (Baranova et al., 2011 J. Biol. Chem. 286, 25675-25686). HA has been implicated in some anti-inflammatory activities (see Day and Milner 2019).

TSG-6 (Tumor Necrosis Factor-Stimulated Gene-6)

TSG-6 is a secreted protein composed of two modular domains. TSG-6 is not usually constitutively expressed in adult tissues, rather being induced in response to inflammatory mediators. During inflammation, TSG-6 is an endogenous protector of tissues. Many of the immunomodulatory and tissue-protective effects of MSCs are mediated by their secretion of TSG-6.

Recombinant full-length TSG-6 protein has been shown to have anti-inflammatory and tissue protective effects in a wide range of disease models, such as atherosclerosis, myocardial infarction, hypertrophic scarring, colitis, auto-immune diabetes, rheumatoid arthritis, traumatic brain injury or acute lung injury.

Full length TSG-6 is hard to make, insoluble and prone to aggregation. As disclosed herein, these disadvantages are not associated with LINK_TSG6, a short recombinant peptide comprising the LINK module of human TSG-6. This short polypeptide is easier to make than full length TSG6, and is highly soluble and stable in solution.

LINK_TSG6 polypeptide as disclosed herein comprises only the Link module of human or mammalian TSG-6. In some embodiments, the TSG-6 polypeptide comprises or consists essentially of the amino acid sequence according to SEQ ID NO: 2 or SEQ ID NO: 5. The Link module corresponds to residues 37-128 of SEQ ID NO:s 2 and 5, and is shown in SEQ ID NO: 7. In some preferred aspects, the LINK_TSG6 polypeptides useful in the present invention do not comprise some or all of residues 1-35 of the full length TSG6 sequence of SEQ ID NO: 2 or 5 at the N terminal, The Link module is responsible for the hyaluronan (HA) binding activity, chondroitin-4-sulfate binding activity, aggrecan binding activity, inter-α-inhibitor (IαI) binding activity, bikunin binding activity, versican binding activity, dermatan sulfate binding activity, pentraxin-3 binding activity, thrombospondin-1 binding activity, thrombospondin-2 binding activity, fibronectin binding activity, heparin/heparan sulfate binding activity, RANKL binding activity of TSG-6, bone morphogenetic protein (BMP)-2 binding activity, BMP-4 binding activity, BMP-5 binding activity, BMP-6 binding activity, BMP-7 binding activity, BMP-13 binding activity, BMP-14 binding activity, CXCL4 binding activity, CXCL6 binding activity, CXCL8 binding activity, CXCL11 binding activity, CXCL12 binding activity, CCL2 binding activity, CCL5 binding activity, CCL7 binding activity, CCL19 binding activity, CCL21 binding activity or CCL27 binding activity.

LINK_TSG6 may be a fragment of TSG-6 exhibiting one or more of hyaluronan (HA) binding activity, chondroitin-4-sulfate binding activity, aggrecan binding activity, inter-α-inhibitor (IαI) binding activity, bikunin binding activity, versican binding activity, dermatan sulfate binding activity, pentraxin-3 binding activity, thrombospondin-1 binding activity, thrombospondin-2 binding activity, fibronectin binding activity, heparin/heparan sulfate binding activity, RANKL binding activity, bone morphogenetic protein (BMP)-2 binding activity, BMP-4 binding activity, BMP-5 binding activity, BMP-6 binding activity, BMP-7 binding activity, BMP-13 binding activity, BMP-14 binding activity, CXCL4 binding activity, CXCL6 binding activity, CXCL8 binding activity, CXCL11 binding activity, CXCL12 binding activity, CCL2 binding activity, CCL5 binding activity, CCL7 binding activity, CCL19 binding activity, CCL21 binding activity or CCL27 binding activity.

The LINK domain of TSG-6 (LINK_TSG6) may be the region of full-length TSG-6 N-terminal to the CUB_C domain. As such, the LINK_TSG6 protein may lack all or part of the CUB_C domain.

The LINK domain may contain the amino acid sequence of SEQ ID NO: 7 or SEQ ID NO: 9. LINK_TSG6 polypeptide comprises, consists, or consists essentially of (i) the amino acid sequence of SEQ ID NO: 7 or SEQ ID NO: 9, or (ii) an amino acid sequence having at least 80% identity to the amino acid sequence of SEQ ID NO: 7 or 9.

LINK_TSG6 is preferably a polypeptide comprising or consisting of: (i) the amino acid sequence of SEQ ID NO: 7 or 9, or (ii) an amino acid sequence having one of at least 80%, 85%, 90%, 91%, 92%, 93%, 94%, 95%, 96%, 97%, 98%, 99% or 100% identity to the amino acid sequence of SEQ ID NO: 7 or 9.

Accordingly, the LINK_TSG6 polypeptide may comprise:
(a) the amino acid sequence of SEQ ID NO: 7;
(b) a variant thereof having at least 50% identity to the amino acid sequence of SEQ ID NO: 7 and having RANKL binding activity; or
(c) a fragment of either (a) or (b) having CXCL4 binding activity, CXCL6 binding activity, CXCL8 binding activity, CXCL11 binding activity, CXCL12 binding activity, CCL2 binding activity, CCL5 binding activity, CCL7 binding activity, CCL19 binding activity, CCL21 binding activity or CCL27 binding activity.

The LINK_TSG6 polypeptide may consists of, or consist essentially of, the sequence shown in SEQ ID NO: 7.

SEQ ID NO: 9 shows a recombinant polypeptide which includes the Link module of TSG-6 (LINK_TSG6).

Accordingly, the TSG-6 polypeptide used in the invention may preferably comprises:
(a) the amino acid sequence of SEQ ID NO: 9;
(b) a variant thereof having at least 50% identity to the amino acid sequence of SEQ ID NO: 9 and having RANKL binding activity; or
(c) a fragment of either (a) or (b) having CXCL4 binding activity, CXCL6 binding activity, CXCL8 binding activity, CXCL11 binding activity, CXCL12 binding activity, CCL2 binding activity, CCL5 binding activity, CCL7 binding activity, CCL19 binding activity, CCL21 binding activity or CCL27 binding activity.

The LINK_TSG6 polypeptide preferably consists of, or consists essentially of, the sequence shown in SEQ ID NO: 9.

In some aspects described herein, the LINK_TSG6 polypeptide is not conjugated to an active agent, such as an antibody or antigen binding fragment. For example, in some cases, the LINK_TSG6 polypeptide is not conjugated to an IL-17A antibody or fragment thereof. In some cases, the LINK_TSG6 polypeptide comprises or consists of a single copy of LINK_TSG6 polypeptide, such as a single copy of SEQ ID NO: 7 or SEQ ID NO:9. In other words, in these cases, the LINK_TSG6 polypeptide does not comprise a plurality of LINK module sequences, such as a plurality of copies of SEQ ID NO: 7 or SEQ ID NO: 9. In some cases, the LINK_TSG6 polypeptide does not comprise a His tag, such as a 6×HIS tag.

Amino acid identity may be calculated using any suitable algorithm. For example the UWGCG Package provides the BESTFIT program which can be used to calculate homology (for example used on its default settings) (Devereux et al. (1984) *Nucleic Acids Research* 12, 387-395). The PILEUP and BLAST algorithms can be used to calculate homology or line up sequences (such as identifying equivalent or corresponding sequences (typically on their default settings), for example as described in Altschul (1993) *J. Mol. Evol.* 36, 290-300; Altschul et al. (1990) *J. Mol. Biol.* 215, 403-10.

Software for performing BLAST analyses is publicly available through the National Center for Biotechnology Information (ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Nat. Acad. Sci.* USA 89, 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90, 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The variant sequences typically differ by at least 1, 2, 5, 10, 20, 30, 50 or more mutations (which can be substitutions, deletions or insertions of amino acids). For example, from 1 to 50, 2 to 30, 3 to 20 or 5 to 10 amino acid substitutions, deletions or insertions can be made. The modified polypeptide may generally retain CXCL4 binding activity, CXCL6 binding activity, CXCL8 binding activity, CXCL11 binding activity, CXCL12 binding activity, CCL2 binding activity, CCL5 binding activity, CCL7 binding activity, CCL19 binding activity, CCL21 binding activity or CCL27 binding activity, preferably in a dose-dependent manner. The substitutions are preferably conservative substitutions, for example according to the following Table. Amino acids in the same block in the second column and preferably in the same line in the third column may be substituted for each other:

| ALIPHATIC | Non-polar | G A P |
| | | I L V |
| | Polar—uncharged | C S T M |
| | | N Q |
| | Polar—charged | D E |
| | | K R |
| AROMATIC | | H F W Y |

A LINK_TSG6 polypeptide used in the invention is typically at least 10, for example at least 15, 20, 25, 30, 40, 50, 60, 70, 80, 90 or more amino acids in length, up to 100, 150, 200 or 250 amino acids in length, as long as it retains the CXCL4 binding activity, CXCL6 binding activity, CXCL8 binding activity, CXCL11 binding activity, CXCL12 binding activity, CCL2 binding activity, CCL5 binding activity, CCL7 binding activity, CCL19 binding activity, CCL21 binding activity or CCL27 binding activity of TSG-6. Preferably, the polypeptide includes the sequence shown in SEQ ID NO: 7. Fragments of the amino acid sequence of SEQ ID NO: 2, SEQ ID NO: 3, SEQ ID NO: 5, SEQ ID NO: 6, SEQ ID NO: 7 or SEQ ID NO: 9 preferably contain the residues shown to be essential for hyaluronan binding in Mahoney et al. (2001) *J. Biol. Chem.* 276, 22764-22771 and Blundell et al. (2003) *J. Biol. Chem.* 278, 49261-49270. Fragments of the amino acid sequence of SEQ ID NO: 2 or 5 preferably contain the residues Lys-46 and/or Tyr-47 and/or Tyr-94 and/or Phe-105 and/or Tyr-113 of SEQ ID NO: 2 or 5. Most preferably, the fragment of SEQ ID NO: 2 or 5 contains each of residues Lys-46, Tyr-47, Tyr-94, Phe-105 and Tyr-113 of SEQ ID NO: 2 or 5.

Fragments of the amino acid sequence of SEQ ID NO: 7 may be used in the invention. Such fragments preferably contain the residues Lys-10 and/or Tyr-11 and/or Tyr-58 and/or Phe-69 and/or Tyr-77 of SEQ ID NO: 7. Most preferably, the fragment of SEQ ID NO: 7 contains each of residues Lys-10, Tyr-11, Tyr-58, Phe-69 and Tyr-77 of SEQ ID NO: 7.

Fragments of the amino acid sequence of SEQ ID NO: 9 preferably contain the residues Lys-11 and/or Tyr-12 and/or Tyr-59 and/or Phe-70 and/or Tyr-78 of SEQ ID NO: 9. Most preferably, the fragment of SEQ ID NO: 9 contains each of residues Lys-11, Tyr-12, Tyr-59, Phe-70 and Tyr-78 of SEQ ID NO: 9. The TSG-6 polypeptides used in the invention may be chemically modified, e.g. post-translationally modified. For example, they may be glycosylated, phosphorylated or comprise modified amino acid residues. They may be modified by the addition of histidine residues to assist their purification or by the addition of a transmembrane sequence to promote insertion into the cell membrane. Such modified polypeptides fall within the scope of the term "polypeptide" used herein.

Suitable assays for determining the ability of a TSG-6 polypeptide to bind to HA, chondroitin-4-sulfate, aggrecan, inter-α-inhibitor (IαI), bikunin, versican, dermatan sulfate, pentraxin-3, thrombospondin-1, heparin/heparan sulfate, fibronectin and RANKL are well-known in the art (Getting et al. (2002) *J. Biol. Chem.* 277, 51068-51076; Mahoney et al. (2005) *J. Biol. Chem.* 280, 27044-27055; Salustri et al. (2004) *Development* 131, 1577-1586; Parkar et al. (1997) *FEBS Lett.* 410, 413-417; Parkar et al. (1998) *FEBS Lett.* 428, 171-176; Mahoney et al. (2001) *J. Biol. Chem.* 276, 22764-22771; Nentwich et al. (2002) *J. Biol Chem.* 211, 15354-15362; Kuznetsova et al. (2005) *J. Biol. Chem.* 280, 30899-30908), Dyer et al. (2014) *J. Immunol* 192, 2177-2185; Dyer et al. (2016) *J. Biol. Chem.* 291, 12627-12640; and Mahoney et al. (2008) *J. Biol. Chem* 283, 25952-25962.

TSG-6 polypeptides for use in the invention may be in a substantially isolated form. It will be understood that the polypeptide may be mixed with carriers or diluents which will not interfere with the intended purpose of the polypeptide and still be regarded as substantially isolated. A polypeptide for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention.

LINK_TSG6 polypeptides for use in the present invention may be natural or non-naturally occurring polypeptides. Polypeptides may be isolated from any suitable organism that expresses a TSG-6 polypeptide. The TSG-6 polypeptide may be isolated from a human or another suitable mammal, such as primates, rats or mice. Alternatively, TSG-6 polypeptide may be isolated from a fish or an amphibian. Polypeptides for use in the invention may also be prepared as fragments of such isolated polypeptides.

Further, the LINK_TSG6 polypeptides may also be made synthetically or by recombinant means. For example, a recombinant LINK_TSG6 polypeptide may be produced by transfecting cells in culture with an expression vector comprising a nucleotide sequence encoding the polypeptide operably linked to suitable control sequences, culturing the cells, extracting and purifying the LINK_TSG6 polypeptide produced by the cells. Methods for the recombinant production of polypeptides are well-known in the art (for example, Sambrook et al., 2001, Molecular Cloning: a laboratory manual, 3$^{rd}$ edition, Cold Harbour Laboratory Press). Preferably, the LINK_TSG6 polypeptide is made in a bacteria, such as E. coli. Preferably, the LINK_TSG6 polypeptide is not made in a CHO cell or other mammalian cell. As will be appreciated by those skilled in the art, proteins and polypeptides made in a bacteria such as E. coli will completely or substantially lack glycosylation, whereas glycosylation is a common feature of proteins and polypeptides made in a mammalian cell such as a CHO cell. In particular, the LINK_TSG6 according to the present disclosure may lack N-linked glycosylation on Asn118 (SEQ ID NO: 2 or SEQ ID NO: 5).

The amino acid sequence of LINK_TSG6 polypeptides for use in the invention may be modified to include non-naturally occurring amino acids or to increase the stability of the compound. When the polypeptides are produced by synthetic means, such amino acids may be introduced during production. The polypeptides may also be modified following either synthetic or recombinant production. In some aspects, the LINK_TSG6 polypeptides described herein do not comprise a polyhistidine tag, such as a 6His tag. In some aspects, the LINK_TSG6 polypeptides described herein do not comprise a polyhistidine tag at the C-terminal of the polypeptide.

LINK_TSG6 polypeptides for use in the invention may also be produced using D-amino acids. In such cases the amino acids will be linked in reverse sequence in the C to N orientation. This is conventional in the art for producing such polypeptides.

A number of side chain modifications are known in the art and may be made to the side chains of the LINK_TSG6 polypeptides, provided that the polypeptides retain corneal defect healing activity.

Ocular Surface Disorders

The present disclosure relates to the treatment or prevention of ocular surface disorders. Ocular surface disorders include Dry Eye Disease (DED), persistent corneal epitheliopathy (non-healing epithelial defects) associated with diabetic keratopathy, neurotrophic keratopathy, exposure keratopathy or limbal deficiency; contact lens-/eye drop-induced epithelial erosions; ocular graft versus host disease (GVHD); Stevens-Johnson syndrome (SJS); toxic epidermal necrolysis (TEN), ocular surface dysfunction in glaucoma patients, corneal wounds resulting from glaucoma surgery recurrent corneal erosion, superficial punctate keratitis, superior limbic keratoconjunctivitis.

Dry Eye Disease

The present disclosure relates to the treatment or prevention of dry eye disease. Dry eye disease (also known as dry eye syndrome, or keratoconjunctivitis sicca) is the condition of having dry eyes, and affects 7-33% of the world population. Dry eye disease occurs when not enough tears are produced (aqueous deficient dry eye disease), or when tears evaporate too quickly (evaporative dry eye disease). Causes include aging (which is known to cause lacrimal grand atrophy and inflammation), infection, exposure to environmental irritants such as smoke, contact lens use, meibomian gland dysfunction, allergies, pregnancy, Sjögren's syndrome, vitamin A deficiency, laser eye treatment, or as a result of medication such as antihistamines, blood pressure medication, hormone replacement therapy and some antidepressants. In some case, dry eye disease occurs from activities that are associated with a reduced blinking rate, such as the use of screens such as computer monitors, smart phones or tablets, televisions or driving. Dry eye disease may result in tiny abrasions on the surface of the eyes (i.e. defects in corneal epithelium. Dry eye disease may result in pathologic changes in the corneal epithelium, such as squamous metaplasia and loss of goblet cells, in severe cases leading to corneal erosion, ulceration, neovascularization and scarring, or thinning and perforation. A diagnosis of dry eye disease may involve standardized dry eye questionnaire (The Ocular Surface Disease Index, or OSDI), a 12-item scale for the assessment of symptoms related to dry eye disease and their effect on vision.

Dry eye disease is a disease resulting from desiccation injury to the ocular surface, or inflammatory damage to the lacrimal gland. It is clinically distinct from other trauma induced ocular disorders such as chemical burn or trauma resulting from direct exposure of the ocular surface to chemicals (such as alcohol), physical or chemical debridement, blunt force trauma to the eye, penetrating eye injury, or other ocular wounding, although these trauma induced ocular conditions may result in the subsequent development of dry eye disease.

Signs and symptoms of dry eye disease include irritation, redness, discharge, easily fatigued eyes and blurred vision. The signs and symptoms range from mild and occasional to severe and continuous, and scarring of the cornea may result if left untreated.

As disclosed herein, the peptide LINK_TSG6 may be used to treat or prevent dry eye disease. Administration of LINK_TSG6 may result in a healing of corneal epithelial defects, an increase in tear production, the suppression of inflammation and/or an increase/preservation in the number of conjunctival goblet cells. The healing of corneal epithelial defects may result in a reduction in the number of corneal epithelial defects or the size of corneal epithelial defects. Preferably, the healing of corneal epithelial defects results in a reduction in the proportion of the corneal surface that comprises corneal epithelial defects.

Corneal epithelial defects are areas of epithelial (outermost corneal layer) loss, and may be due to mechanical trauma, corneal dryness, neurotrophic cornea, post surgical changes or any other of a variety of etiologies. LINK_TSG6 may be used to reduce or repair corneal epithelial defects. The presence or absence of corneal epithelial defects may be determined by scoring. Corneal epithelial defects may be visualised by staining. For example, through the use of lissamine green or fluorescein dye. The stain is applied to the cornea, and the area of epithelial defect is stained, thereby allowing visualisation of a defect.

An increase in tear production may be determined by Schirmer's test or phenol red thread test.

The number of goblet cell in the conjunctiva may be determined by impression cytology. A cellulose acetate filter paper is applied with pressure to the conjunctival surface for collection of superficial layer and subjected to PAS staining to stain mucin-secreting goblet cells. The number of goblet cells is calculated in the PAS-stained slide.

The presence, absence or amount of inflammation at the ocular surface may be determined by observation of conjunctival redness or conjunctival epithelial defects. Inflammation may cause disruption of corneal and conjunctival epithelium.

The level of inflammatory cytokines may be determined in a sample of tear from the patient. Tear samples may be obtained using Schirmer Tear Test strips. Nucleic acid and/or protein may be extracted from the tear strip by incubating the strip in ammonium bicarbonate and acetone. The level of inflammatory cytokines may be quantified or qualified by RT-PCR or ELISA. The inflammatory cytokines may be selected from IFN-γ, TNF-α, IL-1β and IL-6. In some cases, the inflammatory cytokines may be quantified or qualified by immunoassay. In some cases, the level of MMP9 is determined in a semi-quantitative manner (positive, trace, or negative) using an "InflammaDry" kit in human eyes.

The cornea is the transparent front part of the eye that covers the iris, pupil and the anterior chamber. The cornea, with the anterior chamber and lens, refracts light, with the cornea accounting for approximately two-thirds of the eye's total optical power. While the cornea contributes to most of the eye's focusing power, its focus is fixed. The cornea has unmyelinated nerve endings sensitive to touch, temperature and chemicals; a touch of the cornea causes an involuntary reflex to close the eyelid. Because transparency is of prime importance, the healthy cornea does not have or need blood vessels within it. Instead, oxygen dissolves in tears and then diffuses throughout the cornea to keep it healthy. Similarly, nutrients are transported via diffusion from the tear fluid through the outside surface and the aqueous humour through the inside surface. Nutrients also come via neurotrophins supplied by the nerves of the cornea. In humans, the cornea has a diameter of about 11.5 mm and a thickness of 0.5-0.6 mm in the center and 0.6-0.8 mm at the periphery. Transparency, avascularity, the presence of immature resident immune cells, and immunologic privilege makes the cornea a very special tissue.

The methods disclosed herein are particularly concerned with the corneal epithelium, and damage thereto. The corneal epithelium is an exceedingly thin (approximately 50 μm) multicellular epithelial tissue layer (non-keratinized stratified squamous epithelium) of fast-growing and easily regenerated cells, kept moist with tears. The corneal epithelium is made up of epithelial cells and covers the front of the cornea. It acts as a frontline barrier to protect the cornea, resisting the free flow of fluids from the tears, and prevents bacteria from entering the cornea and inside of the eye. Irregularity or defects of the corneal epithelium disrupts the smoothness of the air/tear-film interface, the most significant component of the total refractive power of the eye, thereby reducing visual acuity. It is continuous with the conjunctival epithelium, and is composed of about 6 layers of cells which are shed constantly on the exposed layer and are regenerated by multiplication in the basal layer. In dry eye disease, the corneal epithelium often becomes damaged.

In some methods, tear production is increased, or the thickness of the tear film coating the eye is increased. In some cases, tear retention is decreased, such that tears are evaporated quickly from the eye. Tearing (also known as lacrimation or lachrymation) is the reflex secretion of tears in response to external or internal irritants. Tears are a bodily fluid which may serve to clean and lubricate the eyes in response to irritation. In healthy mammalian eyes, the cornea is continually kept wet and nourished by basal tears. They lubricate the eye, and help to keep it clear of dust. Tear fluid contains water, mucin, lipids, lysozyme, lactoferrin, lipocalin, lacritin, immunoglobulins, glucose, urea, sodium, and potassium. Some of the substances in lacrimal fluid (such as lysozyme) fight against bacterial infection as a part of the immune system. Lysozyme does this by dissolving a layer in the outer coating, called peptidoglycan, of certain bacteria. Tears are a typical body fluid with a salt content similar to blood plasma. Usually, in a 24-hour period, 0.75 to 1.1 grams (0.03-0.04 ounce avoirdupois) of tears is secreted; this rate slows with age. In addition, the basal tears are composed of antioxidants such as ascorbate, urate, cysteine, glutathione, and tyrosine. Ascorbate and urate constitute half of the tears.

A second type of tears results from irritation of the eye by foreign particles, or from the presence of irritant substances such as onion vapors, perfumes and other fragrances, tear gas, or pepper spray in the eye's environment, including the cornea, conjunctiva, or nasal mucosa, which trigger TRP channels in the ophthalmic nerve. It can also occur with bright light and hot or peppery stimuli to the tongue and mouth. It is also linked with vomiting, coughing and yawning. These reflex tears attempt to wash out irritants that may have come into contact with the eye.

The methods disclosed herein may relate to preservation or improvement of tear production, such as basal tears or reflex tears.

Patient Selection

In accordance with the methods of the invention, the methods may additionally comprise the step of selecting a subject for treatment with a therapeutically effective amount of a polypeptide comprising or consisting of LINK_TSG6.

The methods may comprise evaluating a subject or patient for evidence of, or susceptibility to, an ocular surface disorder such as dry eye disease, such as corneal damage (for example the presence of corneal epithelial lesions), inadequate tear production and inflammation (for example redness or swelling, or the presence of one or more biological markers of inflammation such as one or more of the pro-inflammatory cytokines TNFα, IL-1β, IFN-γ or IL-6 and MMP9).

The method may involve a comprehensive eye examination. This may include: assessment of medical history to determine the patient's signs and symptoms and to note any general health problems, medications or environmental factors that may be contributing to the dry eye problem; external examination of the eye, including lid structure and blink dynamics; evaluation of the eyelids and cornea using bright light and magnification; or measurement of the quantity and quality of tears for any abnormalities.

An individual may be determined to have a corneal epithelial defect, for example through staining with lissamine green, rose bengal or fluorescein dye.

The individual may be determined to have inadequate tear production, for example through using the phenol red thread test or Schirmer's test.

In some cases described herein, the individual to be treated has a condition that is associated with increased incidence of ocular surface disorders such as dry eye disease. In some cases the condition is an autoimmune condition. The autoimmune condition may be Sjögren's syndrome. The individual may have been previously diagnosed as having Sjögren's syndrome. Sjögren's syndrome causes one of the most severe forms of dry eye disease, characterised by inflammatory destruction of lacrimal glands and the ocular surface. Inflammation of lacrimal glands and ocular surface is a key feature of dry eye disease, and plays an important role in the pathogenesis of dry eye disease and Sjögren's syndrome. In some cases, the autoimmune condition is rheumatoid arthritis or diabetes. In some cases, the individual has Type 1 diabetes or Type 2 diabetes.

In some cases, the ocular surface disorder such as dry eye disease does not involve inflammation. Dry eye disease not associated with inflammation may be associated with tear film instability and/or fast tear evaporation.

Treatments

Disclosed herein are methods of treating or preventing ocular surface disorders such as dry eye disease. The methods may involve the reduction or elimination of one or more signs and symptoms of an ocular surface disorder such as dry eye disease, such as a reduction in corneal epithelial defects or lesions, an increase in tear production, an increase or preservation of the number of goblet cells, a reduction in the expression of one or more inflammatory cytokines, or a reduction in redness, or burning sensations, pain or discomfort, or an improvement in visual signs and symptoms such as loss of vision or blurring of vision.

The methods may involve the treatment or prevention of corneal epithelial defects or lesions. The methods may result in a decrease in the number and/or extent of corneal epithelial lesions. The methods may result in a decrease in the number and/or extent of corneal epithelial lesions as compared to the number and/or extent of corneal epithelial lesions prior to the treatment. The methods may result in a decrease in the number and/or extent of corneal epithelial lesions as compared to the number and/or extent of corneal epithelial lesions in an untreated control, or a control treated with full length TSG-6, such as TSG-6 comprising or consisting of SEQ ID NO: 3 or SEQ ID NO: 5. The extent of corneal epithelial lesions may be reduced by at least 25%, at least 50%, at least 75%, or at least 100% compared to the control. The treatment may result in corneal epithelial lesions on 0%, less than 10%, less than 20%, less than 30%, less than 40% or less than 50% of the corneal surface.

The methods may involve the treatment or prevention of inadequate tear production. The methods may result in an increase in tear production, such as an increase in the volume of tear production. The methods may result in an increase in the volume of tears produced as compared to the volume of tears prior to the treatment. The methods may result in an increase in the volume of tears produced as compared to the volume of tears in an untreated control, or a control treated with full-length TSG-6, such as TSG-6 comprising or consisting of SEQ ID NO: 3 or SEQ ID NO: 5. The volume of tears may be increased by at least 10%, at least 20%, at least 30%, at least 40%, at least 50%, at least 60%, at least 70%, at least 80%, at least 90%, at least 100% or more than 100% compared to the control.

The methods may involve increasing or preserving the number of goblet cells. In this context, increasing or preserving the number of goblet cells means that the number of goblet cells after treatment with LINK_TSG6 is not decreased to the same extent as the decrease observed in the absence of the treatment, such as in an untreated control. In some cases, the number of goblet cells is increased or unchanged as compared to the number of goblet cells prior to the treatment.

The methods may involve a reduction in the levels of one or more inflammatory cytokines. For example, the method may result in a reduction in the levels of nucleic acids corresponding to one or more inflammatory cytokines. In some cases, the method results in a reduction in the levels inflammatory cytokine proteins. The inflammatory cytokines may be selected from TNFα, IL6, IFN-γ, and IL-1β. The levels may be decreased by 5%, 10%, 15%, 20%, 25%, 30%, 35%, 40%, 45%, 50%, 60%, 70%, 80%, 90% or 100% compared to the level before treatment, or as compared to an untreated control.

Treatment may result in complete resolution of the signs and symptoms of the ocular surface disorder such as dry eye disease.

Prevention may mean that no signs and symptoms of an ocular surface disorder such as dry eye disease emerge, or it may mean that the signs and symptoms of the ocular surface disorder such as dry eye disease develop to a lesser extent than in the absence of treatment.

Methods described herein may involve the topical administration of LINK_TSG6. LINK_TSG6 may be topically administered to the eye (ocular delivery), preferably to the cornea, such as the surface of the cornea. In some cases, the LINK_TSG6 is administered as an eye drop. The LINK_TSG6 may be formulated as a topical liquid formulation, such as an eye drop. LINK_TSG6 may be formulated by suspension or emulsion.

Administration is preferably in a therapeutically effective amount. A therapeutically effective amount of LINK_TSG6 may be determined according to various parameters, especially according to the polypeptide; the age, weight and condition of the patient to be treated; the route of administration; and the required regimen. Again, a physician will be able to determine the required route of administration and dosage for any particular patient. A therapeutically effective amount of LINK_TSG6 is an amount effective to ameliorate one or more signs and symptoms of an ocular surface disorder such as dry eye disease, such as to reduce the level of corneal damage or corneal lesions, increase lacrimal function, or increase lacrimal tear production, or reduce inflammation in the eye, such as inflammation in the cornea.

In some cases, LINK_TSG6 is administered at 12 μg-15 μg per eye, such as between 10 μg and 20 μg, or between 12 and 15 μg. In some cases, LINK_TSG6 is administered at about 8 μg per eye, about 9 μg per eye, about 10 μg per eye, about 11 μg per eye, about 12 μg per eye, about 13 μg per eye, about 14 μg per eye, or about 15 μg per eye.

In some cases, a higher dose is desired. In such cases, LINK_TSG6 is administered at about 120 μg-150 μg per eye. In some cases, the dosage of LINK_TSG6 is at least 80 μg, at least 90 μg, at least 100 μg, at least 110 μg, at least 120 μg, at least 130 μg, or at least 140 μg per eye. In some cases, the dosage of LINK_TSG6 is less than 170 μg, less than 160 μg, less than 150 μg, less than 140 μg, less than 130 μg or less than 120 μg per eye.

In some cases, an even higher dose is desired. For example, the dosage of LINK_TSG6 may be at least 170 μg, at least 180 μg, at least 190 μg, at least 200 μg, at least 210 μg at least 220 μg, at least 230 μg, at least 240 μg, at least 250 μg, at least 260 μg, at least 270 μg, at least 280 μg, at least 290 μg, at least 300 μg, at least 320 μg, at least 340 μg, at least 360 μg, at least 380 μg, least 400 μg, at least 420 μg, at least 440 μg, at least 460 μg, at least 480 μg, at least 500 μg, at least 550 μg, at least 600 μg, at least 650 μg, at least 700 μg, at least 750 μg, at least 800 μg, at least 900 μg, at least 1 mg, at least 1.1 mg, at least 1.2 mg, at least 1.3 mg, at least 1.4 mg, at least 1.5 mg, at least 1.6 mg or at least 1.7 mg.

Administration may be once daily, twice daily, three times daily, four times daily, five times daily, six times daily, seven times daily, eight times daily, nine times daily, ten times daily or more than ten times daily. Administration is preferably twice daily. In some preferred cases, the administration is more than twice daily, such as three or four times daily. In some preferred cases, the administration is less than four times daily, or less than three times daily, or two times daily or once daily. In particularly preferred cases, administration is two times daily. In some cases, the treatment comprises administering LINK_TSG6 polypeptide once per day. In some cases, the treatment comprises administering LINK_TSG6 polypeptide less frequently than once per day, such as once every two days, one time every three days, once every week, or once every two weeks.

The dose, schedule, mode or time course of administration of the polypeptide of the invention can be modified according to response to therapy. For example, dose and/or the frequency of administration and/or time course of administration may be increased if response to therapy is suboptimal. Conversely, dose and/or the frequency of administration and/or time course of administration can be reduced if response to therapy is better than expected.

In some cases, the treatment involves the co-administration of LINK_TSG6 with artificial tears, prednisolone, cyclosporine, XIIDRA® (lifitegrast), or any combination thereof. Administration may be sequential or simultaneous. Preferably, where LINK_TSG6 is co-administered with one or more of prednisolone, cyclosporine, XIIDRA® (lifitegrast) or artificial tears, the administration is simultaneous or substantially simultaneous. Preferably, the co-administered agents are administered via the same route of administration, such as by topical administration to the eye.

Evaluation of a subject for an ocular surface disorder such as dry eye disease may occur at any point before, during or after administration of a therapeutically effective amount of LINK_TSG6. In some embodiments, the methods of the invention comprise commencing administration, evaluating a subject as above and based on the evaluation continuing, altering or discontinuing further administration. In some embodiments, altering administration comprises increasing or decreasing the dose and/or the frequency and/or the time course of administration.

Formulations

Formulations suitable for ocular administration include eye drops wherein the active compound is dissolved or suspended in a suitable carrier, especially an aqueous solvent for the active compound. In preferred formulations, LINK_TSG6 is solubilised in a saline solution. In some formulations LINK_TSG6 is solubilised in PBS (phosphate buffered saline). As described herein, the inventors have discovered that LINK_TSG6 polypeptide has high solubility in saline as compared to full length TSG6. Described herein are compositions, particularly pharmaceutical compositions, comprising high concentrations of LINK_TSG6.

The pharmaceutical composition may comprise LINK_TSG6 polypeptide solubilised in saline. The pharmaceutical composition may comprise LINK_TSG6 polypeptide solubilised in phosphate buffered saline. In some aspects, the pharmaceutical composition comprises at least 2000 µg/ml, 2100 µg/ml, 2200 µg/ml, 2300 µg/ml 2400 µg/ml, 2500 µg/ml, 2600 µg/ml, 2700 µg/ml, 2800 µg/ml, 2900 µg/ml, 3000 µg/ml, 3100 µg/ml, 3200 µg/ml, 3300 µg/ml or more than 3300 µg/ml LINK_TSG6. Preferably, the pharmaceutical formation comprises at least 2000 µg/ml LINK_TSG6.

Eye drop formulations as disclosed herein may further comprise one or more of a preservative, antioxidant, stabilizer, tonicity modifier, viscosity modifier or buffer. Preferably, the eye drop formulation is a sterile eye drop formulation. In some cases, the eye drop formulation contains between about 240 µg/ml and about 300 µg/ml LINK_TSG6. Such formulations are useful for delivering between around 12 µg and around 15 µg of LINK_TSG6 per drop. Each drop may be around 50 µl. The eye drop formulation may comprise between 200 µg/ml and 350 µg/ml, between 200 µg/ml and 320 µg/ml, between 220 µg/ml and 320 µg/ml, or between 240 µg/ml and 300 µg/ml. Preferably, the eye drop formulation comprises between about 240 µg/ml and about 300 µg/ml. The eye drop formulation may contain at least 200 µg/ml, at least 220 µg/ml, at least 230 µg/ml, at least 240 µg/ml, at least 250 µg/ml, at least 260 µg/ml, at least 270 µg/ml, at least 280 µg/ml, at least 290 µg/ml, at least 300 µg/ml, at least 310 µg/ml, at least 320 µg/ml or more than 320 µg/ml LINK_TSG6 polypeptide.

In some cases, a higher dose formulation is desired. Such formulations may contain between 2400 and 3000 µg/ml LINK_TSG6. Such formulations are useful for delivering between around 120 µg and around 150 µg of LINK_TSG6 per drop. The eye drop formulation may comprise between 2000 µg/ml and 3500 µg/ml, between 2000 µg/ml and 3200 µg/ml, between 2200 µg/ml and 3200 µg/ml, or between 2400 µg/ml and 3000 µg/ml. Preferably, the eye drop formulation comprises between about 2400 µg/ml and about 3000 µg/ml. The eye drop formulation may contain at least 2000 µg/ml, at least 2200 µg/ml, at least 2300 µg/ml, at least 2400 µg/ml, at least 2500 µg/ml, at least 2600 µg/ml, at least 2700 µg/ml, at least 2800 µg/ml, at least 2900 µg/ml, at least 3000 µg/ml, at least 3100 µg/ml, at least 3200 µg/ml or more than 3200 µg/ml LINK_TSG6 polypeptide.

In the some cases, the eye drop formulation may further comprise artificial tears. Artificial tears are lubricant eye drops. Artificial tears may contain one or more agents selected from carboxymethyl cellulose, polyvinyl alcohol, hydroxypropyl methylcellulose, hydroxypropyl cellulose, hyaluronan, water, salts and polymers, such as polyethylene glycol or polypropylene glycol.

In some cases, the eye drop formulation may further comprise prednisolone, cyclosporine, XIIDRA® (lifitegrast) or a combination of prednisolone and cyclosporine, prednisolone and XIIDRA® (lifiteqrast), cyclosporine and XIIDRA® (lifitegrast), or prednisolone, cyclosporine and XIIDRA® (lifiteqrast).

Pharmaceutical compositions may be prepared using a pharmaceutically acceptable "carrier" composed of materials that are considered safe and effective. "Pharmaceutically acceptable" refers to molecular entities and compositions that are "generally regarded as safe", e.g., that are physiologically tolerable and do not typically produce an allergic or similar untoward reaction, such as gastric upset, loss, or change, of taste (ageusia) and the like, when administered to a human. In some embodiments, this term refers to molecular entities and compositions approved by a regulatory agency of the US federal or a state government, as the GRAS list under section 204(s) and 409 of the Federal Food, Drug and Cosmetic Act, that is subject to premarket review and approval by the FDA or similar lists, the U.S. Pharmacopeia or another generally recognised pharmacopeia for use in animals, and more particularly in humans.

The term "carrier" refers to diluents, binders, lubricants and disintegrants. Those with skill in the art are familiar with such pharmaceutical carriers and methods of compounding pharmaceutical compositions using such carriers.

The pharmaceutical compositions provided herein may include one or more excipients, e.g., solvents, solubility enhancers, suspending agents, buffering agents, isotonicity agents, antioxidants or antimicrobial preservatives. When used, the excipients of the compositions will not adversely affect the stability, bioavailability, safety, and/or efficacy of the active ingredients, i.e. LINK_TSG6 used in the composition.

Thus, the skilled person will appreciate that compositions are provided wherein there is no incompatibility between any of the components of the dosage form. Excipients may be selected from the group consisting of buffering agents, solubilizing agents, tonicity agents, chelating agents, antioxidants, antimicrobial agents, and preservatives. Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include TWEEN® 60 (Polyethylene glycol sorbitan monostearate), Span 80, cetostearyl alcohol, myristyl alcohol, glyceryl monostearate and sodium lauryl sulfate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

EXAMPLES

Example 1: LINK_TSG6 is More Soluble than Full Length TSG-6

The solubility and aggregation state of full-length TSG-6 and LINK_TSG6 in PBS were compared using UV spectrophotometry and dynamic light scattering (DLS) at a range of concentrations. The LINK_TSG6 was fully soluble at 2 mg/ml and showed no aggregation at 0.4, 0.8, 1.6 or 3.2 mg/ml. The full-length protein had much lower solubility with less than 40% of the protein remaining in solution at 0.4, 0.8, 1.6. and 3.2 mg/ml. The full-length protein was also highly aggregated at 0.2, 0.4, 0.8, 1.6 and 3.2 mg/ml. The DLS measurements were out of range for full-length TSG-6 at 1.6 and 3.2 mg/ml, indicating that aggregates of greater than 25 million Da were being formed.

Example 2: LINK_TSG6 Improves Signs and Symptoms of Dry Eye Disease in a Mouse Model Topical TSG-6 has previously been shown to be as effective in inflammation mediated dry eye disease as cyclosporine eye drops (Kim et al., 2016). To test whether the LINK_TSG6 polypeptide was useful in this indication we investigated its effects in the NOD.B10 mouse model of primary ocular Sjögren's syndrome (spontaneous dry eye disease without diabetes).

NOD.B10.H2$^b$ mice (12 week-old, Jackson Lab), a model for primary ocular Sjögren's syndrome (dry eye disease without diabetes) were treated with topically administered with LINK_TSG6 for 7 days. C57BL/6 mice were used as a negative control, as they do not develop spontaneous dry eye.

Mice were treated by topical application of 1 µg LINK_TSG6, in 10 µl PBS, 4× per day (QID) for 7 days. Mice were anesthetised with an intraperitoneal injection of zolazepam-tiletamine (Zoletil®, Virbac, Carros, France), and either 10 µl LINK_TSG6 or PBS was administered using a pipette. Mice were randomly assigned to treatment groups as follows:

1) Group 1 (Negative control): C57BL/6 mice, 12-week old (n=6, 12 eyes), untreated 2) Group 2 (Positive control): NOD.B10, 12-week old (n=6, 6 eyes)+PBS 10 μl QID 3) Group 3 (Experimental group): NOD.B10, 12-week old (n=8, 8 eyes)+LINK_TSG6 1 μg (in 10 μl PBS) QID.

To assess the effect of treatment on dry eye disease, we undertook the following assays:

1) Corneal epithelial defects by vital staining (with lissamine green) of defect sites and scoring. After applying one drop of 3% lissamine Green B to the inferior lateral conjunctival sac of a mouse, the dye staining of the corneal surface was graded in a blinded manner by two ophthalmologists as per the following ocular staining score system: score 0 for no punctuate staining; score 1 when less than one third of the corneal surface was stained; score 2 when two thirds or less was stained; and score 3 when more than two thirds was stained;

2) Lacrimal tear production examined by phenol red thread test;

3) Inflammatory cytokine expression by real time RT PCR in the cornea and intra-orbital gland; and 4) Conjunctival goblet cell count on PAS-stained conjunctival fornix. The number of PAS-stained cells was counted per 100 μm in four different sections of the eye from the same animal, and the average count was determined in each eye as the goblet cell density.

As shown in FIG. 2A, after LINK_TSG6 treatment, corneal epithelial defects were significantly reduced (p<0.01). There was a significant improvement in corneal epithelial defects between PBS- and Link_TSG6-treated groups (p<0.001).

Figure 2B:
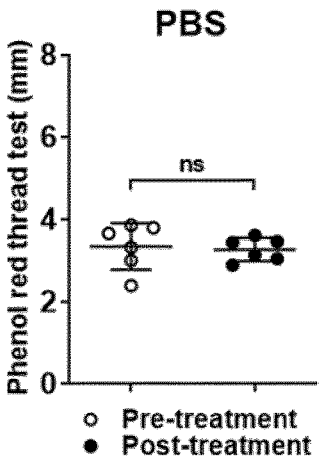
Figure 2B:
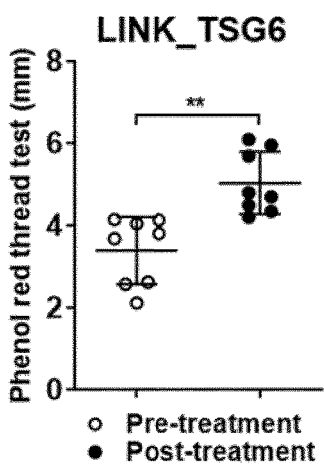
Figure 2B:
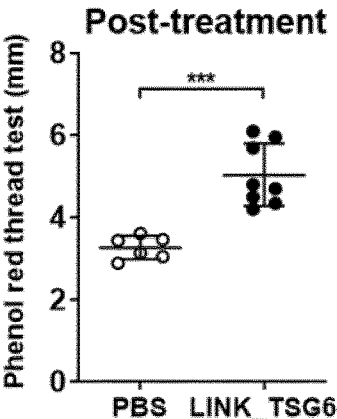

As shown in FIG. 2B, tear production was significantly increased by LINK_TSG6 treatment (p<0.01). There was a significant improvement in tear production between PBS- and LINK_TSG6-treated groups (p<0.001).

Figure 2C:
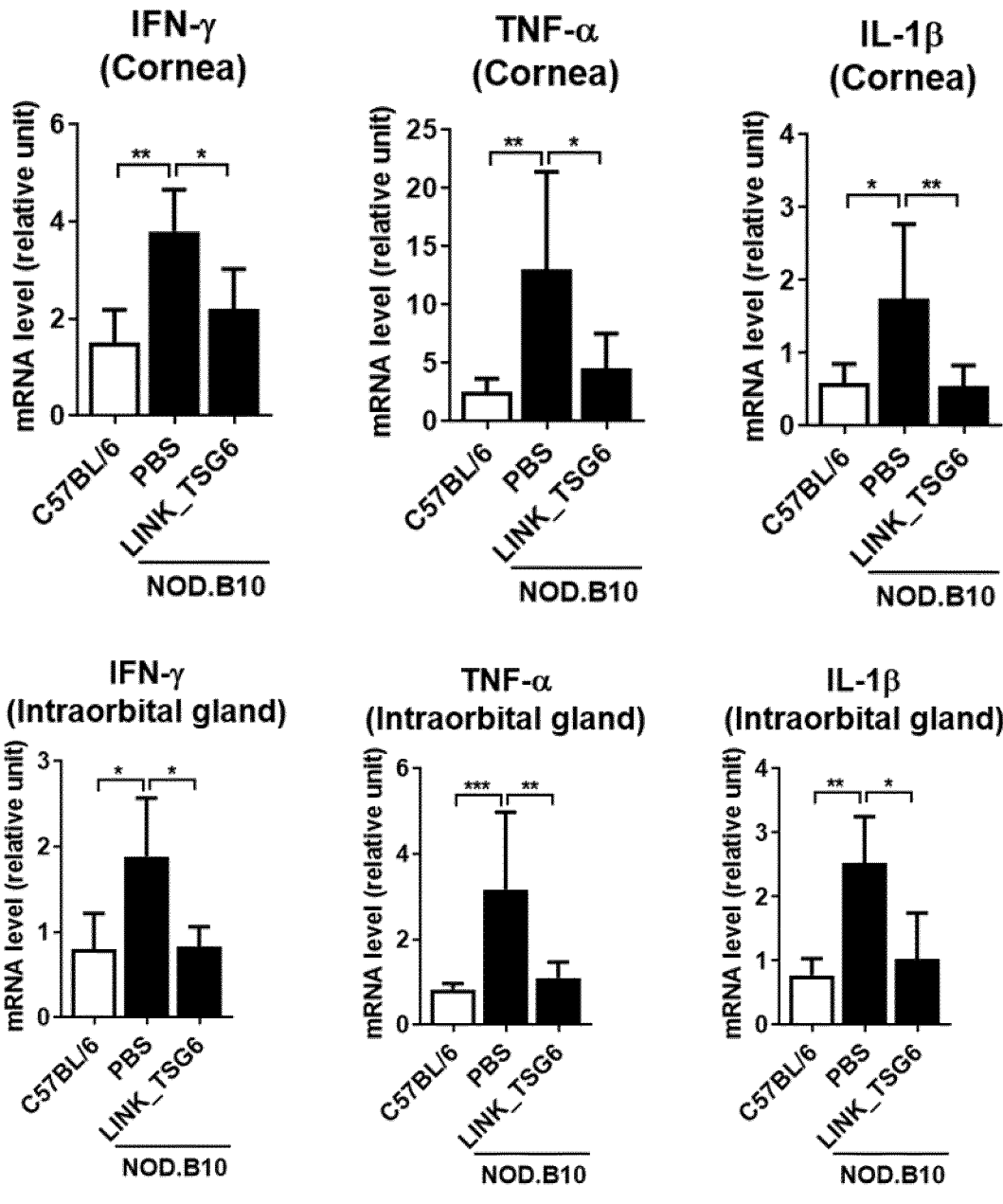
Figure 2D:
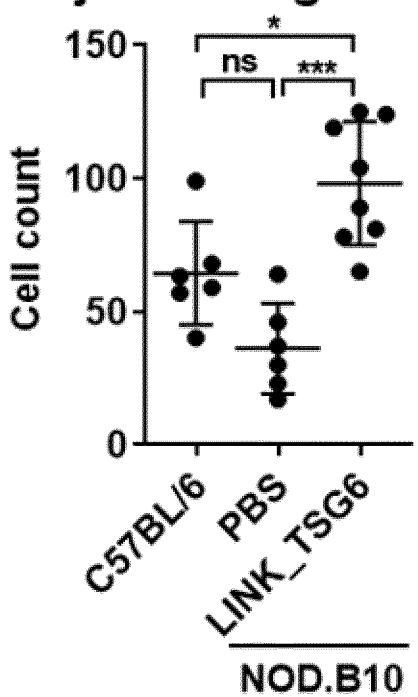

FIG. 2C shows that LINK_TSG6 treatment significantly suppressed mRNA levels of IFN-γ, TNF-α and IL-1β in the cornea and intraorbital gland. LINK_TSG6-treated eyes had levels of cytokines similar to those of control C57BL/6 mice.

2D shows that LINK_TSG6 treatment significantly increased the number of conjunctival goblet cells (these cells produce the mucin components in tears).

Overall, these results demonstrate that LINK_TSG6 significantly suppressed inflammation, reduced corneal epithelial defects, increased tear production, and increased conjunctival goblet cells in NOD.B10 dry eye mice.

Example 3: Effects of LINK_TSG6 on Dry Eye Disease are Dose-Dependent

We were interested to understand whether the effects observed in example 1 were dose dependent. To this end, we applied 1, 0.1, or 0.01 μg of LINK_TSG6, in 5 μl PBS, topically QID for 7 days to 12 week old NOD.B10.H2b mice (Jackson Lab).

Mice were randomly assigned to the following treatment groups:

1) Group 1 (Negative control): C57BL/6 mice, 12-week old (n=6, 12 eyes) untreated 2) Group 2 (Positive control): NOD.B10 (n=8, 8 eyes)+ PBS 5 μl QID 3) Group 3 (Experimental group): NOD.B10 (n=8, 8 eyes)+LINK_TSG6 1 μg (in 5 μl PBS) QID 4) Group 4 (Experimental group): NOD.B10 (n=8, 8 eyes)+LINK_TSG6 0.1 μg QID 5) Group 5 (Experimental group): NOD.B10 (n=8, 8 eyes)+LINK_TSG6 0.01 μg QID The effect of the treatment was determined as per example 1.

Figure 3A:
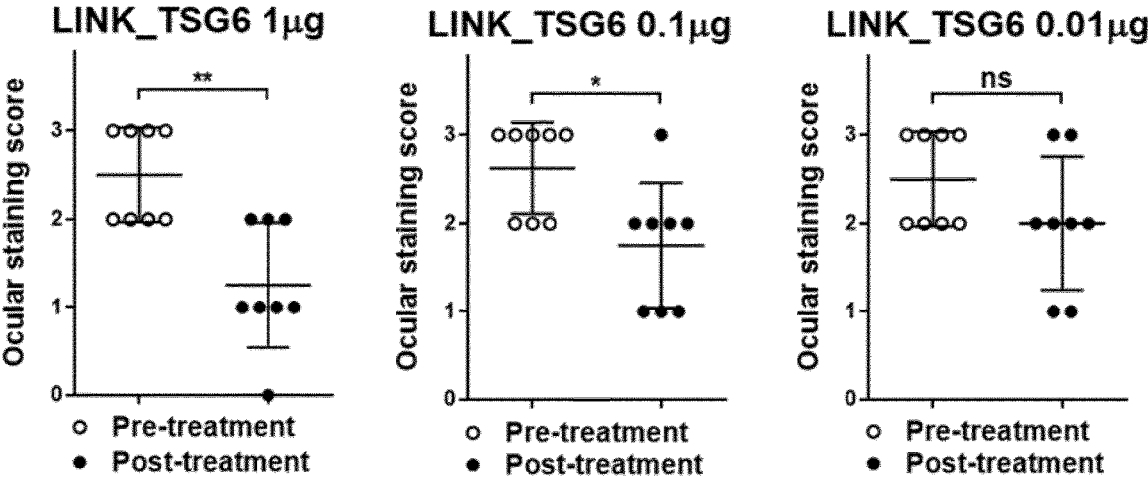
FIG. 3. LINK_TSG6 reduces the signs of dry eye disease in a dose-dependent manner. A. Quantitation of corneal epithelial defects from lissamine green-stained corneas. LINK_TSG6 1 µg and 0.1 µg was effective in reducing corneal epithelial defects, but LINK_TSG6 0.01 µg did not significantly improve corneal epithelial defects. B. Quantification of aqueous tear production by phenol red thread test. LINK_TSG6 1 µg and 0.1 µg were both effective in increasing the amount of tear production, but LINK_TSG6 0.01 µg did not significantly improve tear production. C. Quantification of pro-inflammatory cytokines by real-time RT-PCR analysis. LINK_TSG6 1 µg was most effective in suppressing TNF-α expression. In A and B significance was determined by Wilcoxon matched-pairs signed rank test. *=p<0.05; **=p<0.01; ns=not significant, p>0.05. In C significance was determined by one-way ANOVA and Tukey's multiple comparisons test. ns=not significant, p>0.05; *=p<0.05; =p<0.01 *=p<0.001; ****=p<0.0001.

As shown in FIG. 3A, corneal epithelial defects were quantified in lissamine green-stained corneas. LINK_TSG6 1 μg and 0.1 μg was effective in reducing corneal epithelial defects, but LINK_TSG6 0.01 μg did not significantly improve corneal epithelial defects.

Figure 3B:
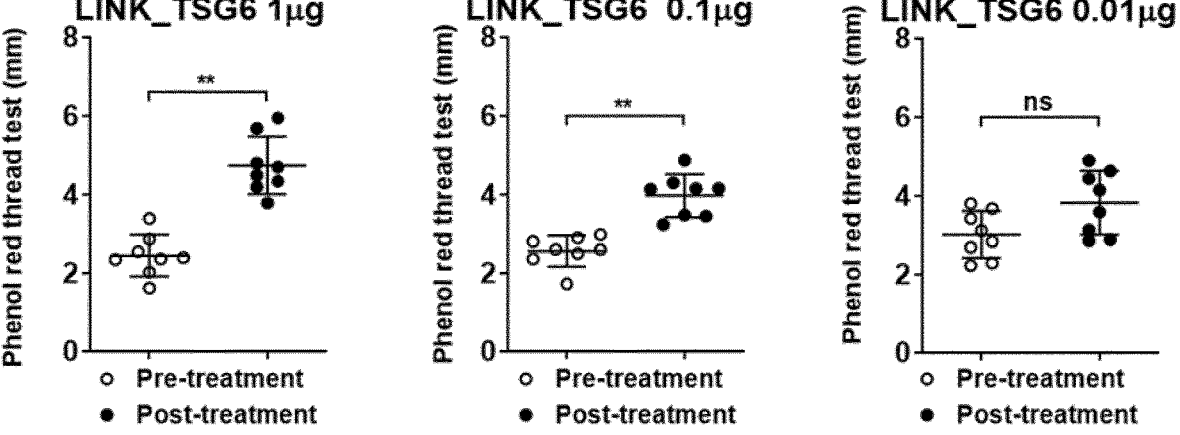

In FIG. 3B, Phenol red threat test indicated that LINK_TSG6 1 μg and 0.1 μg was were effective in increasing the amount of tear production, but LINK_TSG6 0.01 μg did not significantly improve the amount of tear production.

Figure 3C:
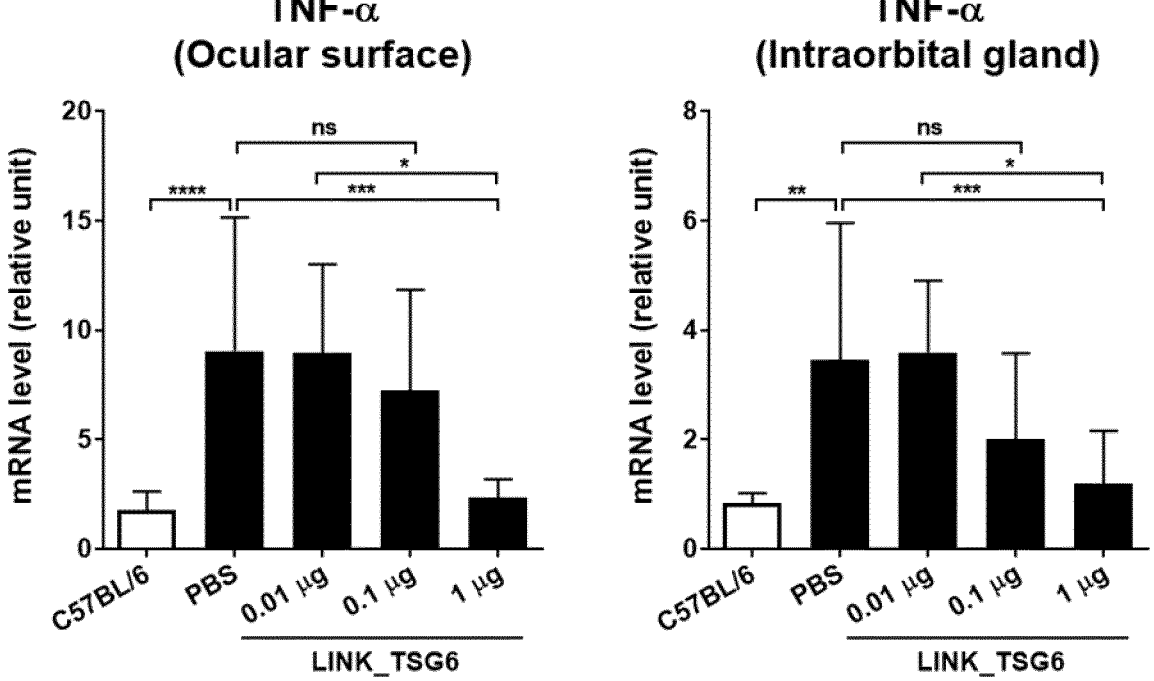

As shown in FIGS. 3C and D, the highest dose of LINK_TSG6 tested, 1 μg was most effective in suppressing TNF-α expression.

Overall, these results demonstrate a dose-dependent improvement of dry eye parameters by topically applied LINK_TSG6 polypeptide (1 μg most effective and 0.01 μg least effective).

Figure 4A:
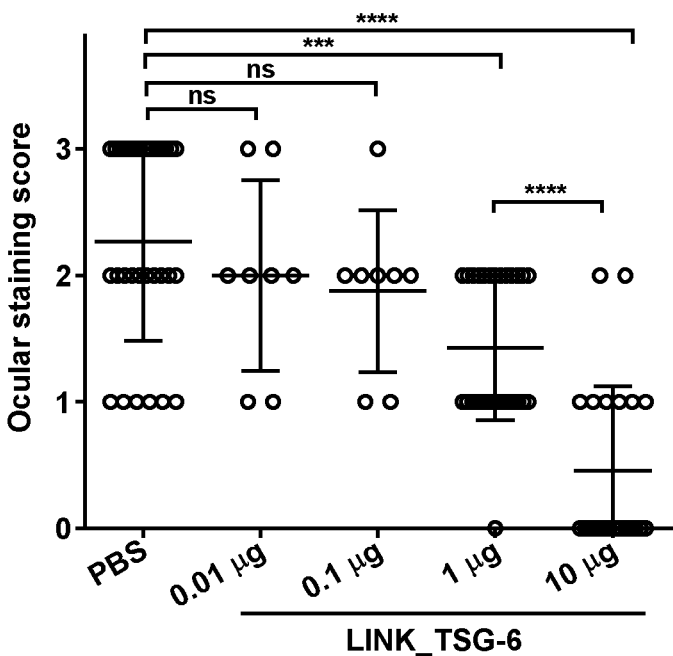
FIG. 4. Dose response data for LINK_TSG6. A. Quantitation of corneal epithelial defects from lissamine green-stained corneas by ocular staining; B. Quantification of aqueous tear production by phenol red thread test; C. Pro-inflammatory cytokine mRNA level as determined by real-time RT-PCR D. Conjunctival goblet cell counts in PAS stained conjunctival sections. Significance determined by one-way ANOVA and Tukey's multiple comparisons tests. ns=not significant, p>0.05; *=p<0.05; =p<0.01 *=p<0.001; ****=p<0.0001.

These effects were also observed with higher doses of LINK_TSG6. As shown in FIG. 4A, the higher doses (1 μg and 10 μg) of LINK_TSG6 exhibited significantly less corneal epithelial damage as compared to PBS-treated mice. At the highest dose, many of the LINK_TSG6 treated eyes have no corneal lesions (score of 0), which is the same as the untreated negative control C57BL/6 mice. This shows that LINK_TSG6 can promote the healing or repair of epithelial lesions.

Figure 4B:
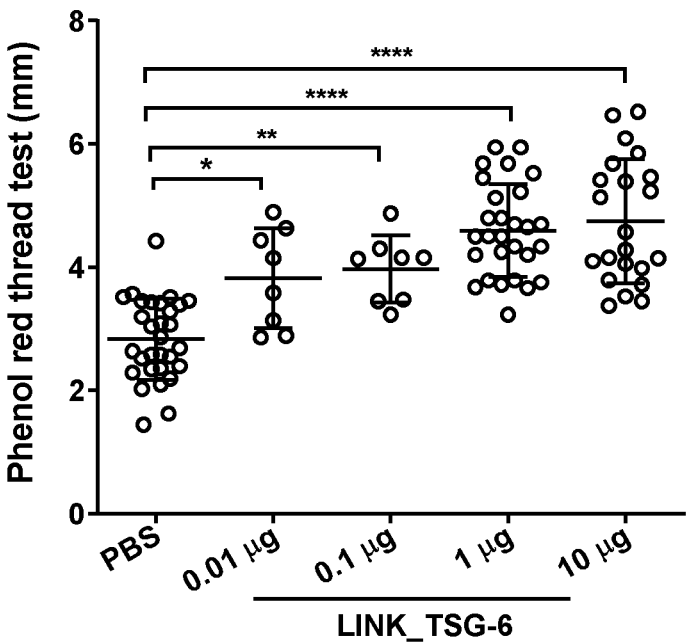
Figure 4C:
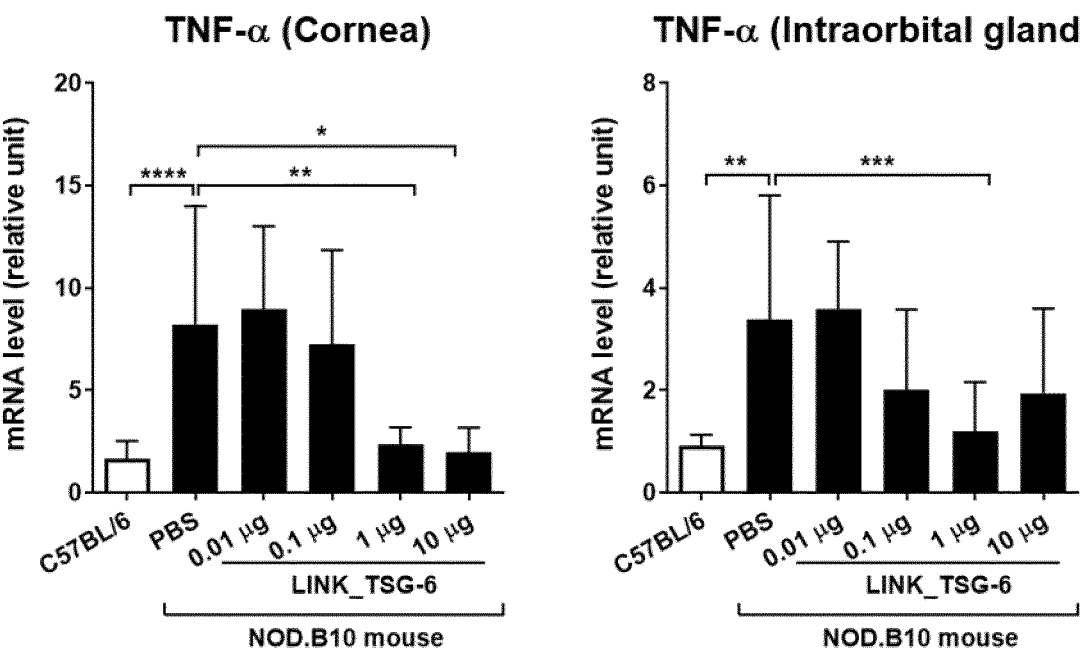
Figure 4D:
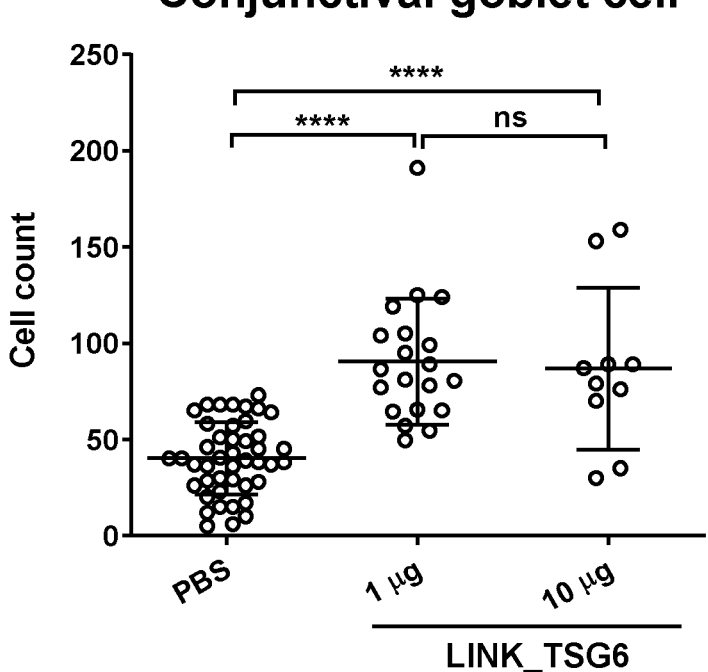

Dose dependent responses were also observed in respect of tear production (FIG. 4B—note that even the lowest dose of LINK_TSG6 tested has a significant effect on tear production), inflammation (FIG. 4C) and conjunctival goblet cell numbers (FIG. 4D).

Example 4: Comparison of Effects of Full Length TSG-6 Protein and LINK_TSG6 on Dry Eye Disease Our experiments revealed that LINK_TSG6 polypeptide was effective at treating dry eye disease. We were interested to understand how this compared to full length (FL) TSG-6 (FL TSG6). We compared equivalent molar doses of FL TSG6 and LINK_TSG6, administered 2×/day (BID).

12 week old NOD.B10 mice and C57BL/6 mice were randomly assigned to treatment groups as follows:

1) Group 1 NOD.B10+PBS 5 μl BID for 7 days (positive control);

2) Group 2 NOD.B10+full-length TSG-6 (FL TSG6) (R&D Systems) 5 μl (3.27, 0.327, 0.0327 μg) BID for 7 days;

3) Group 3 NOD.B10+LINK_TSG6 5 μl (1, 0.1, 0.01 μg) BID for 7 days; and

4) Group 4 C57BL/6 mice (negative control, no dry eye).

Dosages of 0.01, 0.1 and 1.0 micrograms LINK_TSG6 were chosen as per example 2. Mass spectrometry was used to determine the molecular weight of recombinant human TSG-6 (R&D Systems) as 35.7 kDa. Based on this determination, we calculated equimolar doses of 0.037, 0.37 and 3.7 micrograms for full-length TSG-6 (FL TSG6).

Signs and symptoms of dry eye disease were determined as per the previous examples, namely:

1) Lissamine green staining and score for corneal epithelial damage. After applying one drop of 3% Lissamine Green B to the inferior lateral conjunctival sac of a mouse, the dye staining of the corneal surface was graded in a blinded manner by two ophthalmologists as per the following ocular staining score system: score 0 for no punctuate staining; score 0.5 for trace staining;

score 1 when less than one third of the corneal surface was stained; score 2 when two thirds or less was stained; and score 3 when more than two thirds was stained;

2) Phenol red thread test for lacrimal tear secretion
3) Histology (conjunctival PAS staining, lacrimal gland CD3 immunostaining)

Figure 5A:
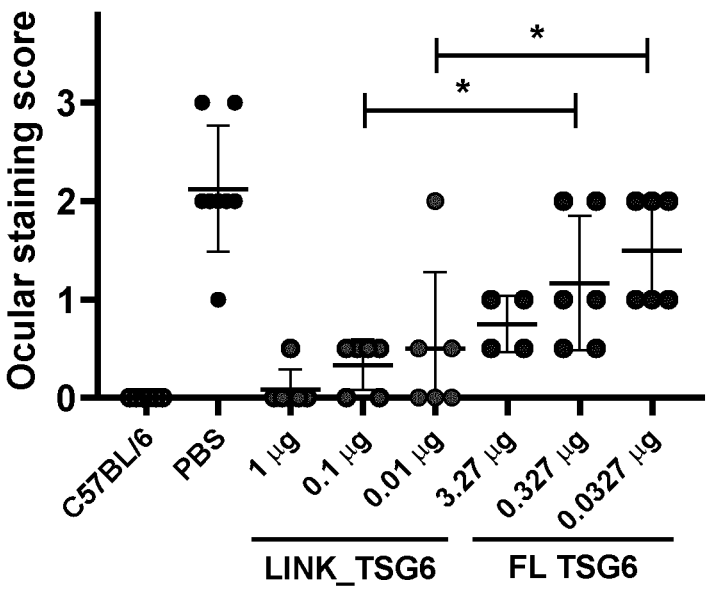
FIG. 5. LINK_TSG6 is more effective than full length human recombinant TSG-6 (FL TSG6) at reducing the signs of dry eye disease. A. Ocular staining score following lissamine green staining; B. Aqueous tear production as determined by phenol red thread test; C. Conjunctival goblet cell counts in PAS stained conjunctival sections D. Histological analysis of CD3 immunostaining in lacrimal gland as expressed by the number of foci with CD3 cell infiltration. Equivalent molar doses are compared (92, 9.2 and 0.92 µmol) corresponding to 1, 0.1 and 0.01 µg LINK_TSG6 and 3.27, 0.327 and 0.0327 µg FL TSG-6, respectively. Significance determined by one-way ANOVA and Tukey's multiple comparisons test. *=p<0.05.

As shown in FIG. 5A, LINK_TSG6 resulted in a significant reduction in corneal epithelial lesions as compared to an equimolar concentration of full length TSG-6.

Figure 5B:
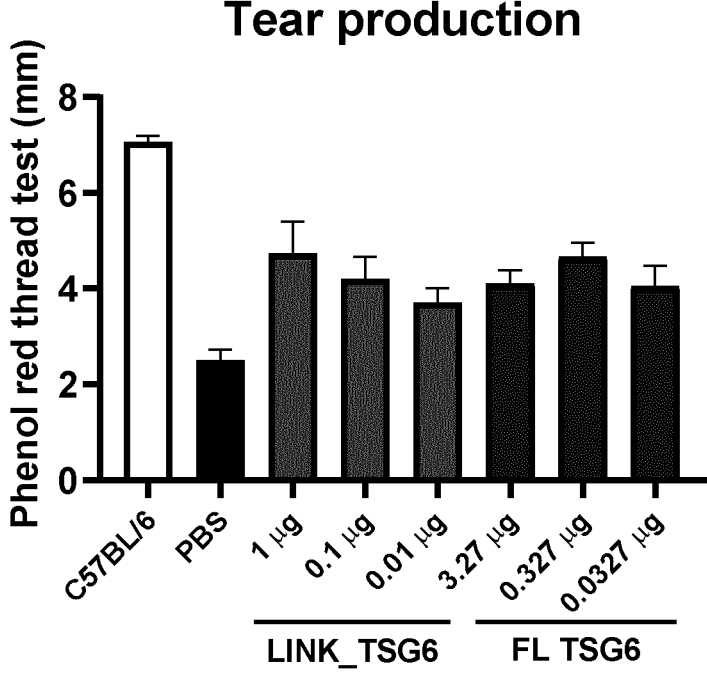
Figure 5C:
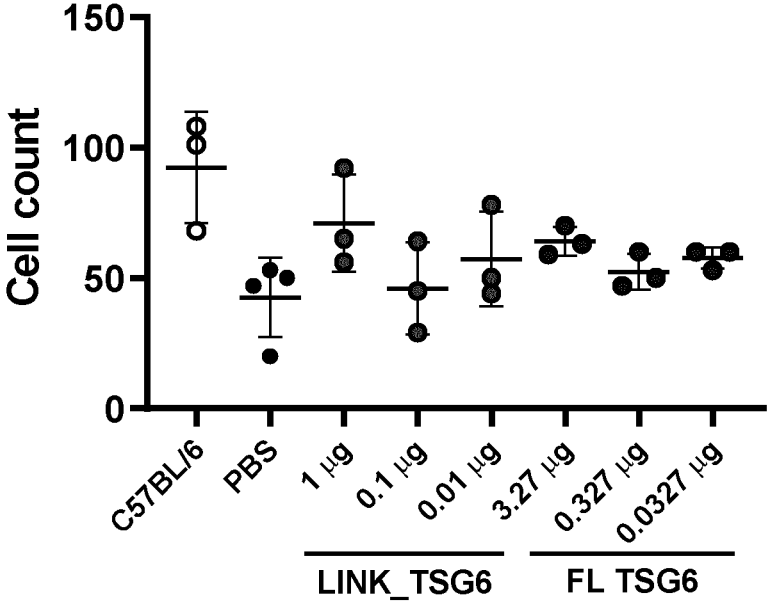
Figure 5D:
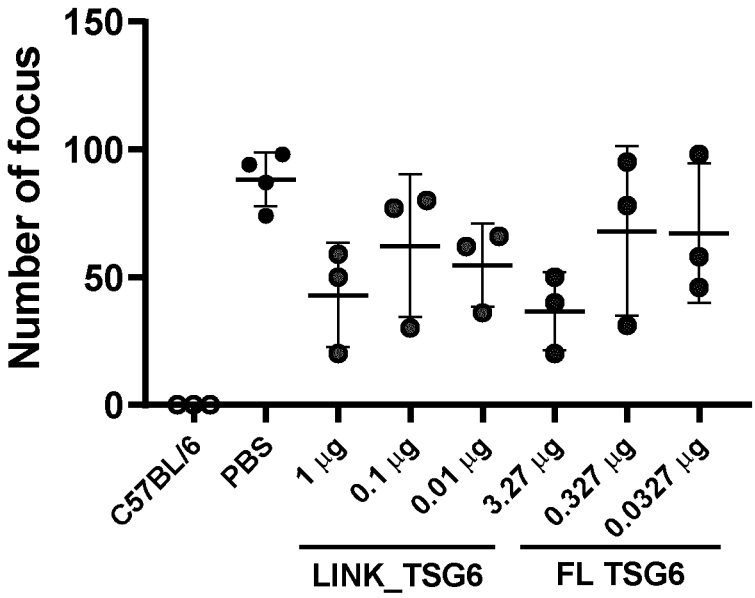

FIGS. 5B, 5C and 5D show that the highest dose tested, 1 µg LINK_TSG6, caused increased tear production, preserved goblet cells and reduced the number of CD3-stained inflammatory foci in the intraorbital gland, as compared to an equimolar dose (3.27 µg) of full length TSG-6.

Example 5: Evaluation of LINK_TSG6 in a Desiccation Injury-Induced Dry Eye Model and Comparison with RESTASIS® (Cyclosporine)

Having demonstrated the efficacy of LINK_TSG6 in the NOD.B10 mouse model of primary ocular Sjögren's syndrome (spontaneous dry eye disease without diabetes), we were interested to understand whether LINK_TSG6 was also effective in treating individuals with the prevalent environmental evaporative dry eye disorder.

We use a desiccation model that better emulates an evaporative dry eye which is more prevalent form of dry eye, compared to the less prevalent Sjögren's syndrome-like dry eye. 7 week-old C57BL/6 mice were kept in a dry chamber and injected intraperitoneally with scopolamine three times daily for 10 days to induce desiccation injury. The air flow from an electric fan was allowed into the cage through the screen for 24 h, and humidity was maintained 30-35% inside the cage. Mice were divided into treatment groups as follows:

1) No desiccation injury (negative control, 2 mice, 4 eyes)
2) Group 1 (5 mice, 10 eyes): Desiccation injury+PBS 5 µl BID for 10 days (positive control)
3) Group 2 (5 mice, 10 eyes): Desiccation injury+ LINK_TSG6 0.1 µg (in PBS 5 µl) BID for 10 days
4) Group 3 (5 mice, 10 eyes): Desiccation injury+ LINK_TSG6 1 µg (in PBS 5 µl) BID for 10 days
5) Group 4 (5 mice, 10 eyes): Desiccation injury+ LINK_TSG6 10 µg (in PBS 5 µl) BID for 10 days
6) Group 5 (5 mice, 10 eyes): Desiccation injury+RESTASIS® (cyclosporine) (0.05% cyclosporine A) 5 µL BID for 10 days After 10 days, signs and symptoms of dry eye were evaluated as follows, 1) Fluorescein staining and score for corneal epithelial damage (C57BL/6 mice are black and fluorescein stain is better for visualization than lissamine green)
2) Phenol red thread test for lacrimal tear secretion
3) Histology (conjunctival PAS staining, lacrimal gland CD3 immunostaining)
4) Molecular assay of ocular surface and lacrimal glands (real time RT-PCR for inflammatory cytokines)

Figure 6A:
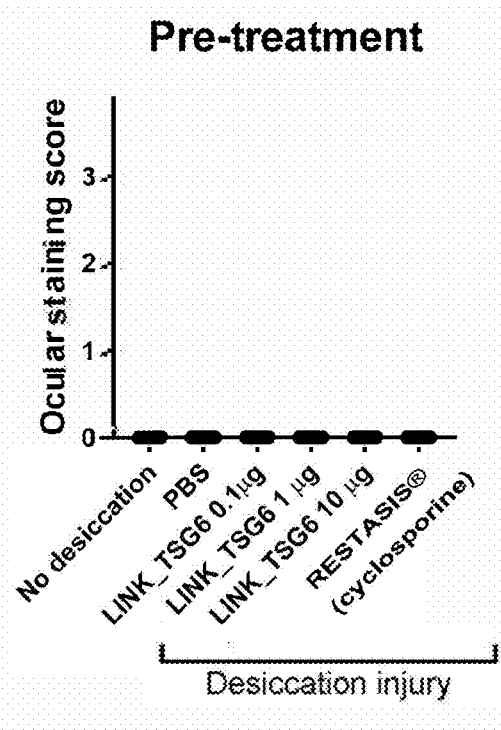
FIG. 6. Evaluation of LINK_TSG6 in a desiccation injury-induced dry eye model and comparison with RESTASIS® (cyclosporine). A. Ocular staining prior to the induction of desiccation injury and pre-treatment; B. Ocular staining post-desiccation injury and post-treatment; C. Tear production prior to the induction of desiccation injury and pre-treatment; D. Tear production post-desiccation injury and post-treatment; E. Th1 cells in draining cervical lymph nodes; F. Th17 cells in draining cervical lymph nodes. ns=not significant, p>0.05; *=p<0.05; =p<0.01 *=p<0.001; ****=p<0.0001.
Figure 6B:
Figure 6B:
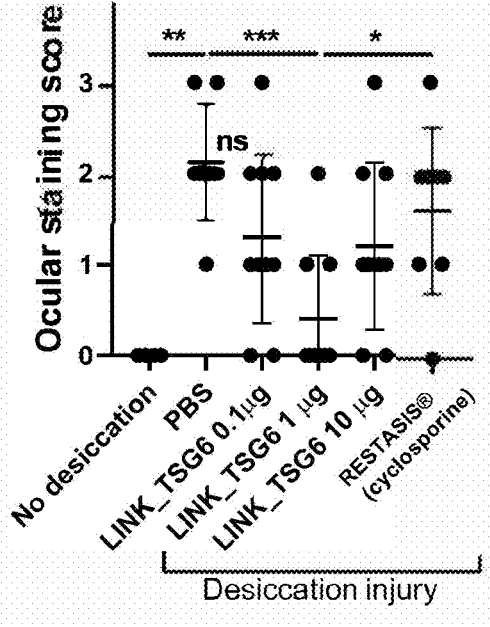
Figures 6C, 6D:
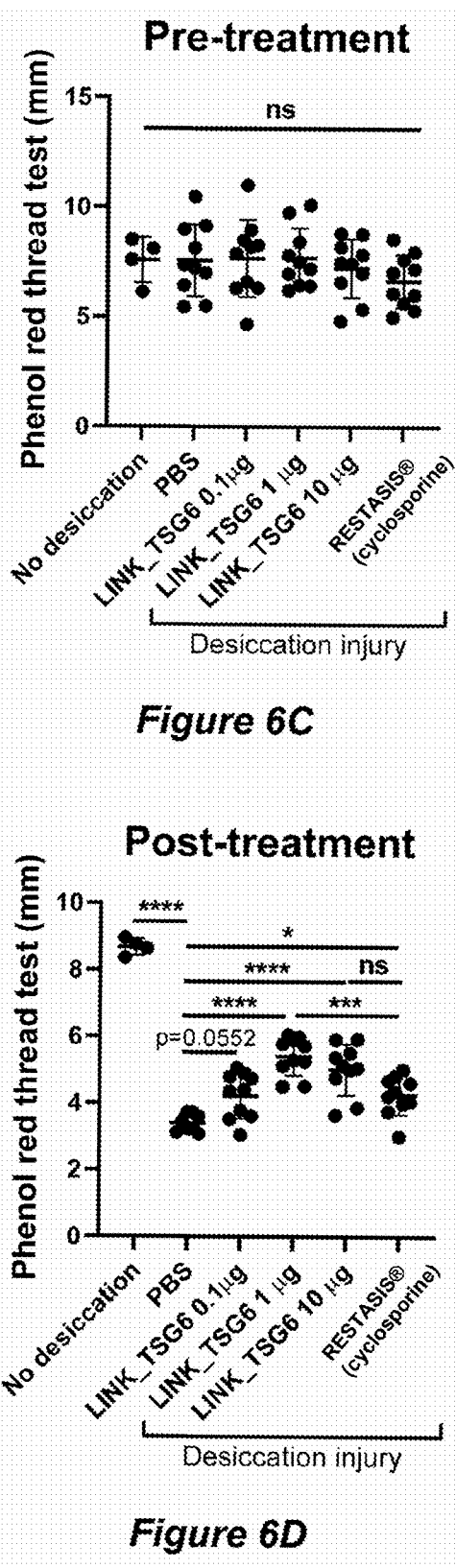

Desiccation injury significantly induced corneal epithelial defects in C57BL/6 mice (p<0.01), as shown in FIG. 6A (pre-desiccation and pre-treatment, showing animals selected for treatment had no corneal lesions at the start of the study) and 6B (post-desiccation and post-treatment), and LINK_TSG6 1 µg was effective at decreasing corneal epithelial defects under desiccation (p<0.001). Interestingly, RESTASIS® (cyclosporine) did not significantly reduce corneal epithelial defects in this model, and LINK_TSG6 1

µg was better at decreasing corneal epithelial defects than RESTASIS® (cyclosporine) (p<0.05). As shown in FIG. 6C (pre-desiccation and pre-treatment) and 6D (post-desiccation and post-treatment), desiccation injury significantly reduced tear production in C57BL/6 mice (p<0.0001). As with the mouse model of primary ocular Sjögren's syndrome, LINK_TSG6 1 µg and 10 µg were effective at preserving tear production under desiccation (p<0.0001), and even 0.1 µg of LINK_TSG6 preserved tear production (p=0.0552). Although RESTASIS® (cyclosporine) was effective at preserving tear production under desiccation (p<0.05), interestingly LINK_TSG6 1 µg was better at preserving tear production than RESTASIS® (cyclosporine) (p<0.001).

Figure 6E:
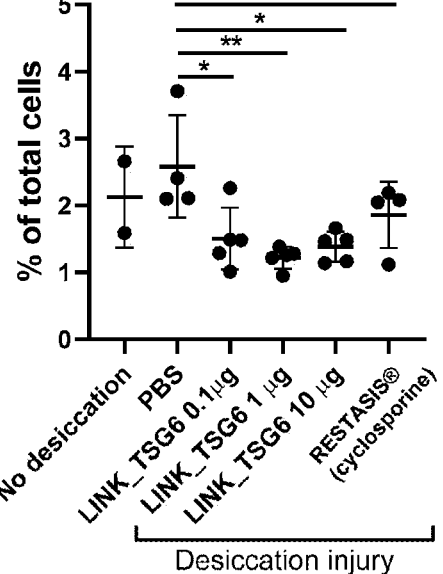
Figure 6F:
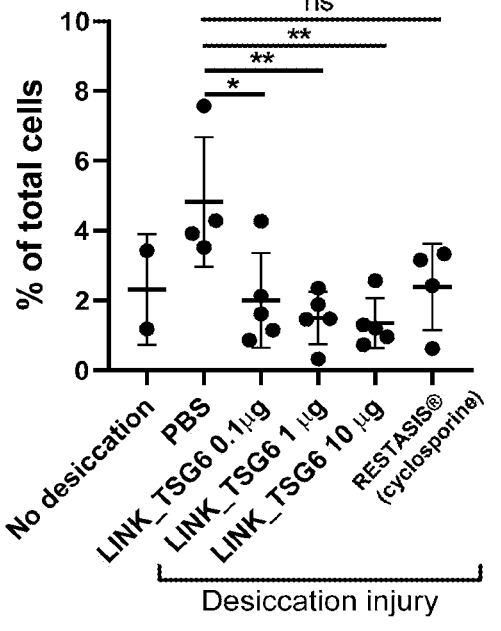

It is well-known that Th1 and Th17 cells are increased in draining cervical lymph nodes (DLN) under desiccation stress, and that these cells are responsible for inducing dry eye. We therefore performed FACS analysis on cervical draining lymph nodes to determine the level of Th1 (IFN-$\gamma^+$CD4$^+$ cells) and Th17 cells (IL17A$^+$CD4$^+$ cells) in response to the various treatments. As shown in FIGS. 6E and 6F, LINK_TSG6 was also effective at suppressing Th1 and Th17 cells in cervical lymph nodes. RESTASIS® (cyclosporine) had no such suppressive effect.

These data therefore indicate that LINK_TSG6 is also effective at treating dry eye disease, including in individuals with the prevalent environmental evaporative dry eye.

Example 6: Evaluation of LINK_TSG6 in Established Desiccation Injury-Induced Dry Eye Having demonstrated that LINK_TSG6 is effective at treating dry eye disease, including in individuals with the prevalent environmental evaporative dry eye, we were interested to understand whether LINK_TSG6 was also effective in treating individuals with established dry eye, to reverse the effects of the disease.

We used the same desiccation model as in Example 5, this time allowing the dry eye disease to become established for one week prior to treatment with LINK_TSG6. LINK_TSG6 was applied to the ocular surface after desiccation injury had been exerted to the ocular surface. The mice were then kept in the dry chamber with scopolamine injections for the 10 further days during which the treatments were administered.

7 week-old C57BL/6 mice were kept in a dry chamber and injected intraperitoneally with scopolamine three times daily for 7 days to establish dry eye. Mice were divided into treatment groups as follows:

1) No desiccation injury (negative control, 2 mice, 4 eyes)
2) Group 1 (5 mice, 10 eyes): Desiccation injury+PBS 5 µl BID for 10 days (positive control)
3) Group 2 (5 mice, 10 eyes): Desiccation injury+ LINK_TSG6 0.1 µg (in PBS 5 µl) BID for 10 days
4) Group 3 (5 mice, 10 eyes): Desiccation injury+ LINK_TSG6 1 µg (in PBS 5 µl) BID for 10 days
5) Group 4 (5 mice, 10 eyes): Desiccation injury+ LINK_TSG6 10 µg (in PBS 5 µl) BID for 10 days.

Signs and symptoms of dry eye disease were determined as per the previous examples, namely:

1) Fluorescein staining and score for corneal epithelial damage (B6 mice are black and fluorescein stain is better for visualization than lissamine green);
2) Phenol red thread test for lacrimal tear secretion; and
3) Histology (conjunctival PAS staining, lacrimal gland CD3 immunostaining).

Figure 7A:
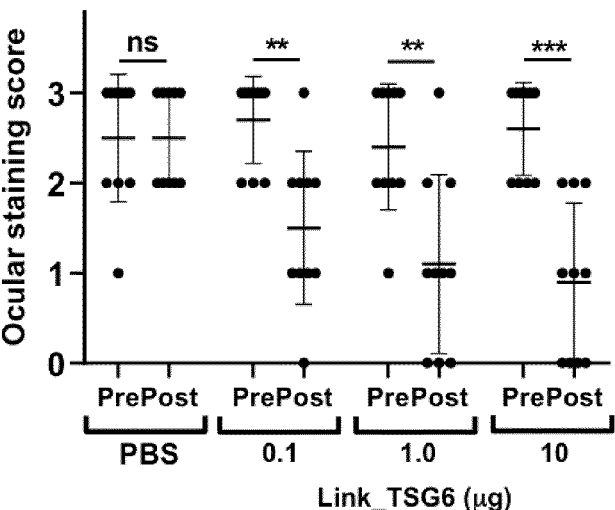
FIG. 7. Evaluation of LINK_TSG6 in already-desiccated mice. A. Ocular staining; B. Tear production; C. Conjunctival goblet cell counts in PAS stained conjunctival sections following treatment; D. MMP-9 mRNA levels at the ocular surface; ns=not significant, p>0.05; *=p<0.05; =p<0.01 *=p<0.001; ****=p<0.0001. A&B Wilcoxon matched-pairs signed rank test for comparison between pre- and post-treatment. C&D one-way ANOVA and Tukey's multiple comparisons test.
Figure 7B:
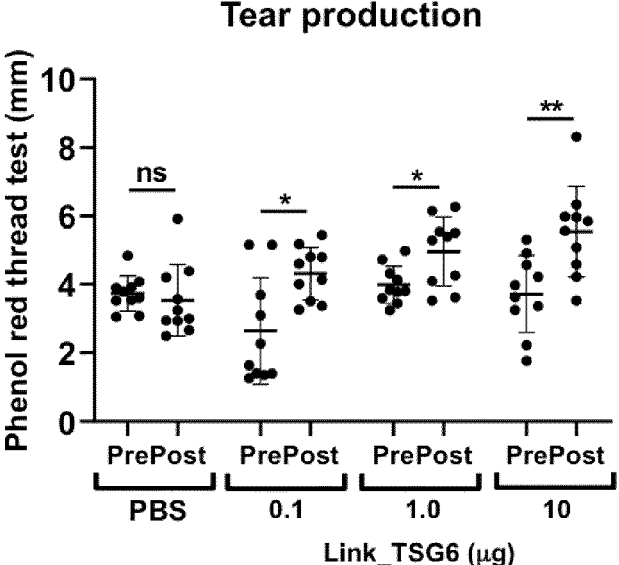

As shown in FIG. 7A LINK_TSG6 was effective at decreasing corneal epithelial defects at all concentrations tested. As shown in FIG. 7B, at all concentrations tested, LINK_TSG6 was effective at increasing aqueous tear production. Significant changes were observed even for the lowest concentration tested.

Figure 7C:
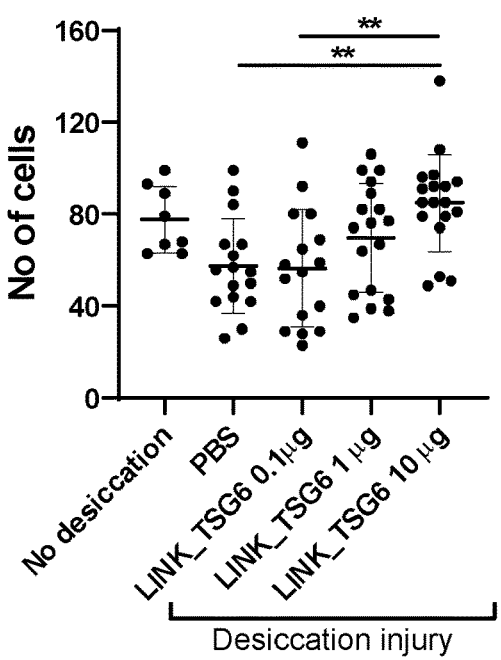

FIG. 7C demonstrates that 1 μg and 10 μg of LINK_TSG6 resulted in an increase in goblet cell number as compared to control, restoring to levels comparable to those observed in the absence of desiccation.

Figure 7D:
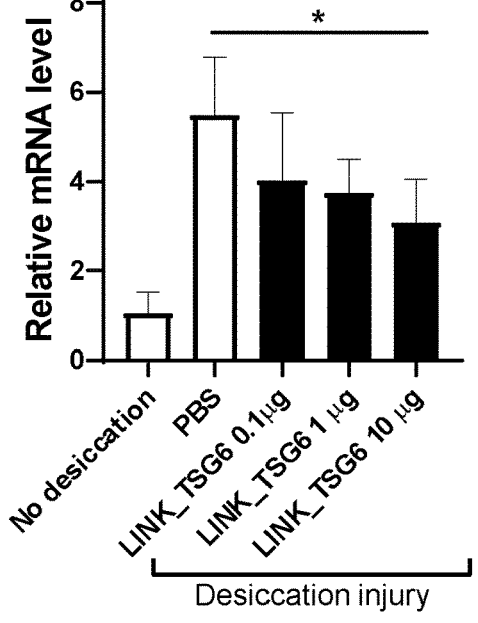

Moreover, as shown in FIG. 7D, treatment with LINK_TSG6 was effective at suppressing the level of MMP-9 mRNA in the ocular surface.

These data therefore indicate that LINK_TSG6 is effective at treating established dry eye disease, in addition to reducing the severity of desiccation injury. These data support the use of LINK_TSG6 for the treatment of individuals with dry eye disorder, including in individuals with the prevalent environmental evaporative dry eye.

Example 7: Evaluation of LINK_TSG6 in a Dry Eye Model and Comparison with RESTASIS® (Cyclosporine)

Having demonstrated the superiority of LINK_TSG6 to RESTASIS® (cyclosporine) in treating evaporative dry eye, we were interested to compare LINK_TSG6 to RESTASIS® (cyclosporine) in the NOD.B10 mouse model of primary ocular Sjögren's syndrome (spontaneous dry eye disease without diabetes), as used in Example 4.

12 week old NOD.B10 mice and C57BL/6 mice were randomly assigned to treatment groups as follows:

1) Group 1 C57BL/6 mice (negative control, no dry eye/desiccation).
2) Group 2 NOD.B10+PBS 5 μl BID for 7 days (positive control);
3) Group 3 NOD.B10+LINK_TSG6 5 μl (0.1, 1, 10 μg/5 μl) BID for 7 days; and
4) Group 4 NOD.B10+RESTASIS® (cyclosporine) 5 μl BID for 7 days;

Signs and symptoms of dry eye disease were determined as per the previous examples, namely:

1) Lissamine green staining and score for corneal epithelial damage.
2) Phenol red thread test for lacrimal tear secretion
3) Histology (conjunctival PAS staining, lacrimal gland CD3 immunostaining)

Figure 8A:
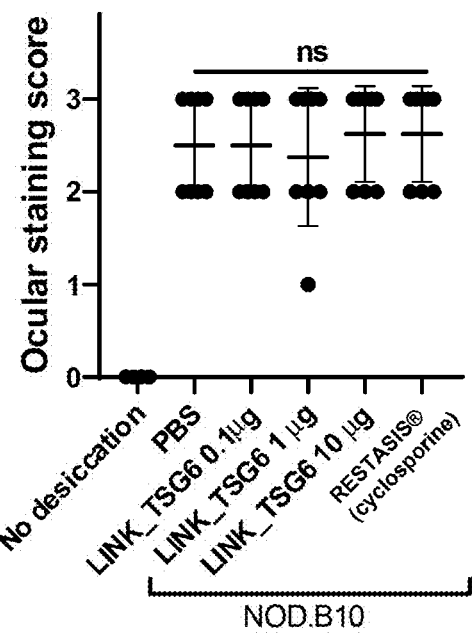
FIG. 8. Comparison of LINK_TSG6 and RESTASIS® (cyclosporine) in a dry eye disease model. A. Ocular staining score following lissamine green staining, prior to treatment; B. Ocular staining score following lissamine green staining following treatment; C. Quantification of aqueous tear production by phenol red thread test pre-treatment D. Quantification of aqueous tear production by phenol red thread test post-treatment E. Conjunctival goblet cell counts in PAS stained conjunctival sections following treatment. F. Histological analysis of CD3 immunostaining in lacrimal gland. ns=not significant, p>0.05; *=p<0.05; =p<0.01 *=p<0.001; ****=p<0.0001, one-way ANOVA and Tukey's multiple comparisons test.
Figure 8B:
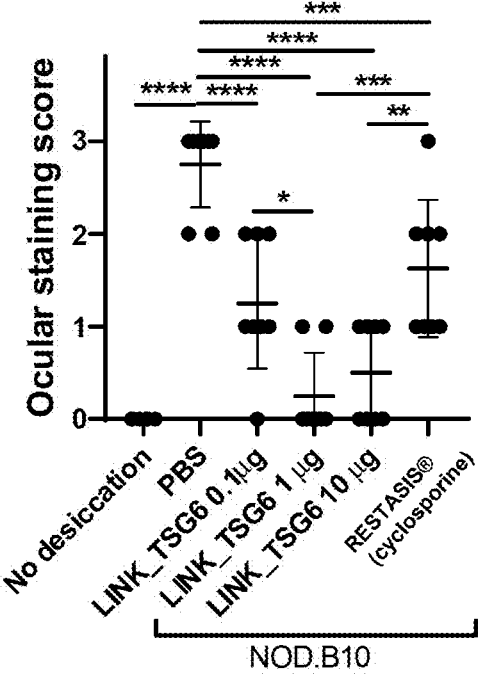
Figure 8C:
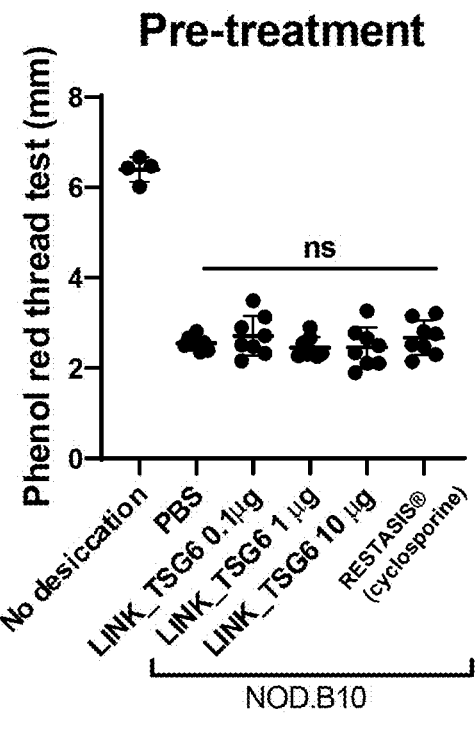
Figure 8D:
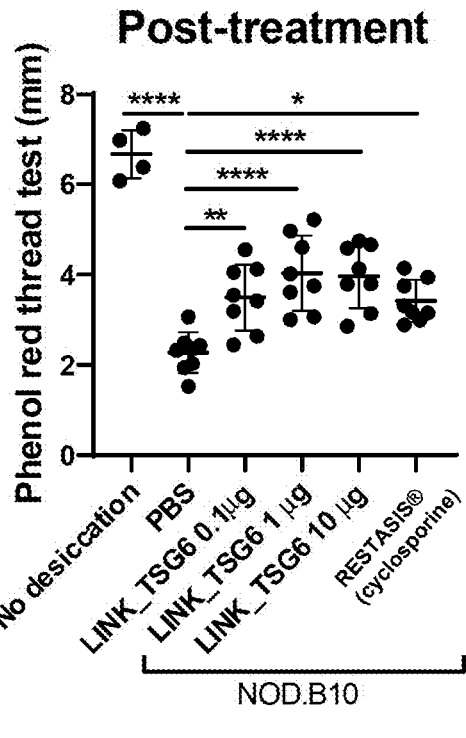
Figure 8E:
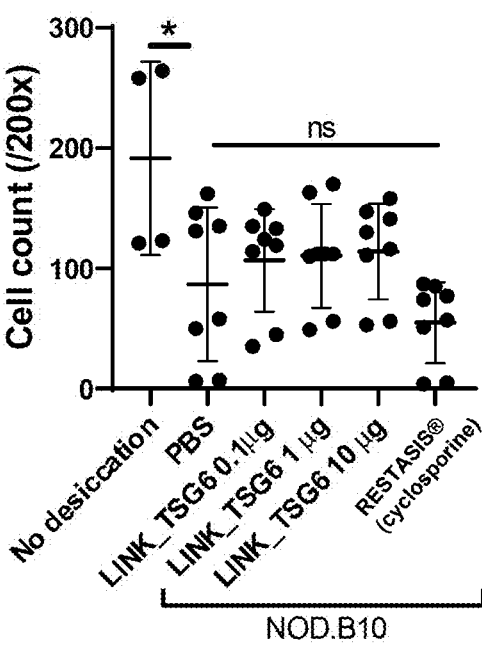
Figure 8F:
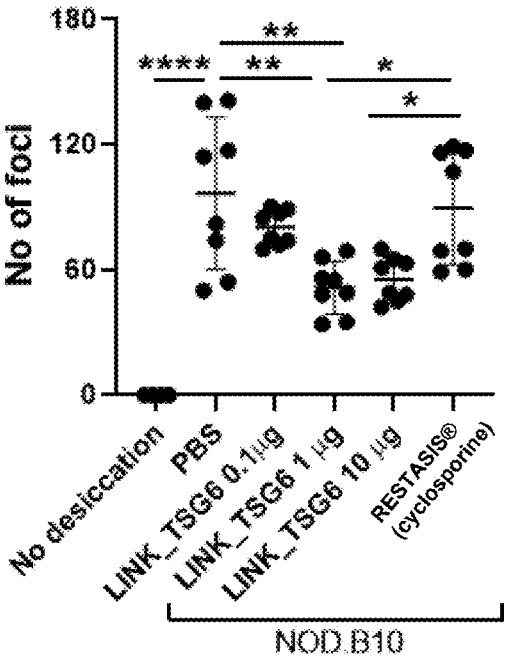

As shown in FIGS. 8B and D, and in agreement with our studies in Example 4, LINK_TSG6 resulted in a significant reduction in corneal epithelial lesions and increase in tear production in the NOD.B10 mouse model of primary ocular Sjögren's syndrome. Moreover, LINK_TSG6 promoted healing to a greater extent than RESTASIS® (cyclosporine) at both the 1 and 10 μg doses, resulting in reduced corneal lesions, preservation in the number of goblet cells, and reduced number of CD3-stained inflammatory foci in the intraorbital gland, as compared to RESTASIS® (cyclosporine). This shows that even at the lowest doses tested, LINK_TSG6 was better at treating dry eye in the NOD.B10 mouse model of primary ocular Sjögren's syndrome (spontaneous dry eye disease without diabetes) than RESTASIS® (cyclosporine), as previously observed in preventing the development of, or treating established, evaporative dry eye disease. These data further support the use of LINK_TSG6 for the treatment of individuals with dry eye disorder.

The invention claimed is:

1. A method for treating dry eye disease (DED) in a subject, comprising administering topically to the subject one or more eye drops, wherein the one or more eye drops comprise an effective amount of a polypeptide comprising a Link module from Tumour necrosis factor-stimulated gene 6 (LINK_TSG6), wherein the LINK_TSG6 consists of (i) the amino acid sequence of SEQ ID NO: 7 or SEQ ID NO: 9, or (ii) the amino acid sequence having at least 90% identity to the amino acid sequence of SEQ ID NO: 7 or 9 and up to 100 amino acids in length; and wherein the treating comprises healing of a corneal epithelial defect, and wherein healing of the corneal epithelial defect is determined by a decrease in ocular staining score as compared to (i) the subject prior to the administering or (ii) an untreated control.

2. The method according to claim 1, wherein the method provides one or more effects selected from the group consisting of:

an increase in tear production;

suppression of inflammation; and a higher number of conjunctival goblet cells.

3. The method according to claim 1, wherein the method comprises administering the one or more eye drops two times per day.

4. The method according to claim 1, wherein the method comprises administering the one or more eye drops less than four times per day.

5. The method according to claim 1, wherein the method further comprises co-administration with one or more of prednisolone, cyclosporine, Lifitegrast or artificial tears.

6. The method according to claim 1, wherein the method comprises administering to the subject the one or more eye drops comprising about 10-200 µg of the polypeptide per eye.

7. The method according to claim 2, wherein the suppression of inflammation comprises a decrease in production of one or more pro-inflammatory cytokines in the subject's cornea or intraorbital lacrimal glands; wherein the pro-inflammatory cytokines are optionally selected from TNF-α, IL-6, IFN-γ and IL-1β.

8. The method according to claim 1, wherein the subject has Sjögren's syndrome.

9. The method according to claim 6, wherein the method comprises administering to the subject the one or more eye drops comprising 120-150 µg of the polypeptide per eye.

*     *     *     *     *